United States Patent
Baldwin et al.

(10) Patent No.: US 9,382,563 B2
(45) Date of Patent: Jul. 5, 2016

(54) EXPRESSION OF GRANULAR STARCH HYDROLYZING ENZYME IN TRICHODERMA

(71) Applicant: Danisco US Inc., Palo Alto, CA (US)

(72) Inventors: Toby M. Baldwin, Palo Alto, CA (US); Benjamin S. Bower, Newark, CA (US); Nigel Dunn-Coleman, El Sauzal (ES); Suzanne E. Lantz, San Carlos, CA (US); Michael J. Pepsin, Castro Valley, CA (US)

(73) Assignee: DANISCO US INC., Palo Alto, CA (US)

( * ) Notice: Subject to any disclaimer, the term of this patent is extended or adjusted under 35 U.S.C. 154(b) by 0 days.

(21) Appl. No.: 14/097,168

(22) Filed: Dec. 4, 2013

(65) Prior Publication Data

US 2014/0179007 A1    Jun. 26, 2014

Related U.S. Application Data

(60) Division of application No. 11/960,259, filed on Dec. 19, 2007, now Pat. No. 8,679,815, which is a division of application No. 11/633,309, filed on Dec. 4, 2006, now Pat. No. 7,335,503, which is a continuation of application No. 10/992,187, filed on Nov. 18, 2004, now Pat. No. 7,262,041.

(60) Provisional application No. 60/566,358, filed on Apr. 28, 2004, provisional application No. 60/531,953, filed on Dec. 22, 2003, provisional application No. 60/524,279, filed on Nov. 21, 2003.

(51) Int. Cl.

| | |
|---|---|
| *C12N 9/34* | (2006.01) |
| *C12N 1/20* | (2006.01) |
| *C12N 1/00* | (2006.01) |
| *C12N 15/00* | (2006.01) |
| *C12P 21/06* | (2006.01) |
| *C07H 21/04* | (2006.01) |
| *C12P 19/14* | (2006.01) |
| *C12N 1/14* | (2006.01) |
| *C12N 9/30* | (2006.01) |
| *C12P 19/20* | (2006.01) |
| *C12P 19/24* | (2006.01) |
| *C12P 19/02* | (2006.01) |
| *C12P 19/04* | (2006.01) |

(52) U.S. Cl.
CPC . *C12P 19/14* (2013.01); *C12N 1/14* (2013.01); *C12N 9/242* (2013.01); *C12N 9/2428* (2013.01); *C12P 19/02* (2013.01); *C12P 19/04* (2013.01); *C12P 19/20* (2013.01); *C12P 19/24* (2013.01); *Y02E 50/17* (2013.01); *Y02P 20/52* (2015.11)

(58) Field of Classification Search
None
See application file for complete search history.

(56) References Cited

U.S. PATENT DOCUMENTS

| | | |
|---|---|---|
| 3,236,687 A | 2/1966 | Smith et al. |
| 3,249,514 A | 5/1966 | Bode |
| 4,092,434 A | 5/1978 | Yoshizumi et al. |
| 4,316,956 A | 2/1982 | Lutzen |
| 4,514,496 A | 4/1985 | Yoshizumi et al. |
| RE32,153 E | 5/1986 | Tamura et al. |
| 4,587,215 A | 5/1986 | Hirsh |
| 4,618,579 A | 10/1986 | Dwiggins et al. |
| 4,863,864 A | 9/1989 | Ashikari et al. |
| 5,028,539 A | 7/1991 | Ingram et al. |
| 5,246,853 A | 9/1993 | Clarkson et al. |
| 5,424,202 A | 6/1995 | Ingram et al. |
| 5,475,101 A | 12/1995 | Ward et al. |
| 5,482,846 A | 1/1996 | Ingram et al. |
| 5,487,989 A | 1/1996 | Fowler et al. |
| 5,514,583 A | 5/1996 | Picataggio et al. |
| 5,554,520 A | 9/1996 | Fowler et al. |
| 5,650,322 A | 7/1997 | Clarkson et al. |
| 5,665,585 A | 9/1997 | Torkkeli et al. |
| 5,874,276 A | 2/1999 | Fowler et al. |
| 6,022,725 A | 2/2000 | Fowler et al. |
| 6,268,328 B1 | 7/2001 | Mitchinson et al. |

FOREIGN PATENT DOCUMENTS

| | | |
|---|---|---|
| CN | 1301307 A | 6/2001 |
| EP | 0171218 B1 | 10/1993 |
| EP | 0625577 A1 | 11/1994 |
| EP | 0244234 B2 | 11/2001 |
| EP | 0215594 B2 | 10/2003 |
| WO | WO 92/00381 | 1/1992 |
| WO | WO 92/06209 | 4/1992 |
| WO | WO 99/01545 | 1/1999 |
| WO | WO 99/28488 | 7/1999 |
| WO | WO 99/60136 | 11/1999 |
| WO | WO 00/04136 | 1/2000 |
| WO | WO 00/75296 | 12/2000 |
| WO | WO 03/068976 | 8/2003 |

OTHER PUBLICATIONS

Verdoes et al. Molecular genetic strain improvement for the overproduction of fungal proteins by filamentous fungi, Appl Microbiol Biotechnol (1995), 43: 195-205.*

Schrickx et al. Growth and product formation in chemostat and recycling cultures by Aspergillus niger N402 and a glucoamylase overproducing transformant, provided with multiple copies of the glaA gene, Journal of General Microbiology (1993), 139: 2801-2810.*

Allison, Daniel S. et al., <<Transformation of the thermophilic fungus *Humicola grisea* var. *thermoidea* and overproduction of *Humicola* glucoamylase,>> Current Genetics, vol. 21, pp. 225-229, 1992.

Altshul, Stephen F. et al., <<Gapped BLAST and PSI-BLAST : A New Generation of Protein Database Search Programs,>> Nucleic Acids Research, vol. 25, No. 17, pp. 3389-3402, 1997.

(Continued)

*Primary Examiner* — Iqbal H Chowdhury

(74) *Attorney, Agent, or Firm* — Danisco US Inc.

(57) ABSTRACT

The present invention relates to filamentous fungal host cells and particularly *Trichoderma* host cells useful for the production of heterologous granular starch hydrolyzing enzymes having glucoamylase activity.

19 Claims, 13 Drawing Sheets

(56) References Cited

OTHER PUBLICATIONS

Arasaratnam, Vasanthi et al., <<Synergistic Action of α-Amylase and Glucoamylase on Raw Corn,>> Starch/Starke vol. 45, No. 6, pp. 231-233, 1993.
Ashikari, Toshihiko et al., <<*Rhizopus* Raw-Starch-Degrading Glucoamylase : Its Cloning and Expression in Yeast,>> Agric. Biol. Chem., vol. 50, No. 4, pp. 957-964, 1986.
Bennett, J. W. et al., ed., <<More Gene Manipulations in Fungi,>> Academic Press, San Diego, pp. 70-76, 1991.
Berka, R.M., et al., GenBank Accession No. Q12623, created Nov. 1996.
Bhikhabhai, Ramagauri et al., <<Isolation of Celluloytic Enzymes from *Trichoderma reesei*, QM 9414,>> Journal of Applied Biochemistry, vol. 6, pp. 336-345, 1984.
Boel, E. et al., <<Glucoamylases G1 and G2 from *Aspergillus niger* are synthesized from two different but closely related mRNAs,>> The EMBO Journal, vol. 3, No. 5, pp. 1097-1102, 1984.
Boel, E. et al., <<Two Different Types of Intervening Sequences in the Glucoamylase Gene From *Aspergillus niger*,>> The EMBO Journal, vol. 3, No. 7, pp. 1581-1585, 1984.
Brumbauer, Aniko et al., <<Fractionation of Cellulase and B-Glucosidase in a *Trichoderma reesei*,>> Bioseparation, vol. 7, pp. 287-295, 1999.
Campbell, Edward I. et al., <<Improved Transformation Efficiency of *Aspergillus niger*,>> Current Genetics, vol. 16, pp. 53-56, 1989.
Cao, Qing-Na et al., <<Penicillopepsin-JT2, A Recombinant Enzyme From *Penicillium janthinellum* and The Contribution of a Hydrogen Bond in Subsite $S_3$ to $k_{cat}$,>> Protein Science, vol. 9, pp. 991-1001, 2000.
Cees, A. M. et al., <<Heterologous Gene Expression in Filamentous Fungi,>> *More Gene Manipulations in Fungi*, Bennett, J.W. et al., ed., pp. 396-428, Academic Press, 1991.
Chen, Hsiu-mei et al., <<Identification and Elimination by Site-Directed Mutagenesis of Thermolabile Aspartyl Bonds in *Aspergillus awamori* Glucoamylase,>> Protein Engineering, vol. 8, No. 6, pp. 575-582, 1995.
Chen, Hsiu-mei et al., <<Effect of Replacing Helical Glycine Residues With Alanines on Reversible and Irreversible Stability and Production of Aspergillus Awamori Glucoamylase,>> Protein Engineering, vol. 9, No. 6, pp. 499-505, 1996.
Chen, Frank Y. et al., <<Regulation of Mammalian Ribonucleotide Reductase R1 Mrna Stability is Mediated by a Ribonucleotide Reductase R1 Mrna 3-Untranslated Region Cis-Trans Interaction Through a Protein Kinase C-Controlled Pathway,>> Biochem. J., vol. 302, pp. 125-132, 1994.
Abstract No. 45, Berka, R. et al. <<Cloning of a Thermostable Glucoamylase from the Thermophilic Fungus Humicola Grisea (var. *Thermoidea*) and its Expression in Aspergillus Niger. Development of a Transformation System for H. Grisea and Use of an Automated Screening Procedure for the Isolation of Mutants of H. Grisea with Enhanced Glucoamylase Secretion, presented at EMBO—Alko Workshop, Molecular Biology of Filamentous Fungi, Hanasaari Conference Centre, Espoo, Finland, Jul. 2-7, 1989.
Poster entitled, Cloning of a Thermostable Glucoamylase from the Thermophilic Fungus Humicola Grisea (var. *Thermoidea*) and its Expression in Aspergillus Niger. Development of a Transformation System for H. Grisea and Use of an Automated Screening Procedure for the Isolation of Mutants of H. Grisea with Enhanced Glucoamylase Secretion, presented at EMBO—Alko Workshop, Molecular Biology of Filamentous Fungi, Hanasaari Conference Centre, Espoo, Finland, Jul. 2-7, 1989.
Database UniProt 'Online !, Nov. 1, 1994, Glucoamylase,>> XP002325133, retrieved from EBI accession No. UNIPROT:Q12623.
Davis, Rowland H. et al., <<Genetic and Microbiological Research Techniques for *Neurospora crassa*,>> *Methods in Enzymology*, 17A, pp. 79-143, 1970.
Ellouz, S. et al., <<Analytical Separation of *Trichoderma reesei*, Cellulases by Ion-Exchange Fast Protein Liquid Chromatography,>> Journal of Chromatography, vol. 396, pp. 307-327, 1987.

Fagerstrom, Richard, <<Purification and Specificity of Recombinant *Hormoconis resinae* Glucoamylase P and Endogenous Glucoamylase From *Trichoderma reesei*,>> Enzyme Microb. Technol., vol. 16, pp. 36-42, 1994.>>.
Finkelstein, David B. et al., ed., *Biotechnology of Filamentous Fungi*, ,>>_ Technology and Products, Chapter 6, pp. 113-156, Butterworth-Heinemann, Boston, MA, 1992.
Fliess, A. et al., <<Characterization of Cellulases by HPLC Separation,>> Eur. J. Appl. Microbiol. Biotechnol., vol. 17, pp. 314-318, 1983.
Flor, Perfecto Q. et al., <<Production and Characteristics of Raw Starch-Digesting Glucoamylase O from a Protease-Negative, Glycosidase-Negative *Aspergillus awamori* var. *kawachi* Mutant,>> Applied and Environmental Microbiology, vol. 34, No. 3, pp. 905-912, Mar. 1983.
Fujii, M. et al., Synergistic Action of Alpha Amylase and Glucoamylase on Hydrolysis of Starch,>> *Biotechnology and Bioengineering*, 27: 260-265, 1985.
Fujii, Michihiro et al., <<Synergism of α-Amylase and Glucoamylase on Hydrolysis of Native Starch Granules,>> Biotechnology and Bioengineering, vol. 32, pp. 910-915, 1988.
Goedegebuur, Frits et al., <<Cloning and Relational Analysis of 15 Novel Fungal Endoglucanases From Family 12 Glycosyl Hydrolase,>> Current Genetics, vol. 41, pp. 89-98, 2002.
Goto, Masatoshi et al., <<The Mechanism of Binding of Glucoamylase I from *Aspergillus awamori* var. *kawachi* to Cyclodextrins and Raw Starch,>> Biosci. Biotech. Biochem., vol. 58, No. 1, pp. 49-54, 1994.
Goyal, Anil et al., <<Characteristics of Fungal Cellulases,>> Bioresource Technology, vol. 36, pp. 37-50, 1991.
Harkki, Anu et al., <<Genetic Engineering of *Trichoderma* to Produce Strains With Novel Cellulase Profiles,>> Enzyme Microb. Technol., vol. 13, pp. 227-233, Mar. 1991.
Harkki, A. et al., <<A Novel Fungal Expression System : Secretion of Active Calf Chymosin from the Filamentous Fungus *Trichoderma reesei*,>> Bio/Technology, vol. 7, pp. 596-603, Jun. 1989.
Hata, Yoji et al., <<The Glucoamylase cDNA from *Aspergillus oryzae* : Its Cloning, Nucleotide Sequence, and Expression in *Saccharomyces cerevisiae*,>> Agric. Biol. Chem., vol. 55, No. 4, pp. 941-949, 1991.
Hayashida, Shinsaku et al. <<High Concentration-Ethanol Fermentation of Raw Ground Corn,>> Agric. Biol. Chem., vol. 46, No. 7, pp. 1947-1950, 1982.
Hayashida, Shinsaku et al., <<Raw Starch-digestive Glucoamylase Productivity of Protease-less Mutant from *Aspergillus awamori* var. *kawachi*,>> Agric. Biol. Chem., vol. 45, No. 12, pp. 2675-2681, 1981.
Hayashida, Shinsaku et al., <<Molecular Cloning of the Glucoamylase I Gene of *Aspergillus awamori* var. *kawachi* for Localization of the Raw-starch-affinity Site,>> vol. 53, No. 4, pp. 923-929, 1989.
Hayashida, Shinsaku et al., <<Raw Starch-digestive Chitin-immobilized Amylase from a Protease-Glycosidase-less Mutant of *Aspergillus awamori* var. *kawachi*,>> Agric. Biol. Chem., vol. 46, No. 6, pp. 1639-1645, 1982.
Ilmen, Marja et al., <<Regulation of Cellulase Gene Expression in the Filamentous Fungus Trichoderma reesei,>> Applied and Environmental Microbiology, vol. 63, No. 4, pp. 1298-1306, 1997.
Innis, M. A. et al., <<Expression, Glycosylation, and Secretion of an *Aspergillus* Glucoamylase by *Saccharomyces cerevisiae*,>> Science, vol. 228, pp. 21-26, 1985.
Jensen, Bo et al., <<Purification of extracellular amylotic enzymes from the thermophilic fungus *Thermomyces lanuginosus*,>> Can. J. Microbiol., vol. 34, pp. 218-223.
Joutsjoki et al., <<Construction by One-step Gene Replacement of *Trichoderma reesei* Strains that Produce the Glucoamylase P of Hormoconis Resinae,>>Curr Genet, Nov.-Dec. 1994, vol. 26, No. 5-6, pp. 422-429.
Karakatsanis, A., et al., "Hydrolysis of various starches by the synergistic action of alpha-amylase and glucoamylase in aqueous two phase impeller agitated systems." Starke-Starch, 49(5): 194-199, 1997.

(56) References Cited

OTHER PUBLICATIONS

Kelly, Joan M. et al., <<Transformation of *Aspergillus niger* by the *amdS* gene of *Aspergillus nidulans*,>> The EMBO Journal, vol. 4, No. 2, pp. 475-479, 1985.
Kinghorn, et al., <<*Applied Molecular Genetics of Filamentos Fungi*, Blackie Academic and Professional, Chapman and Hall, London, 1992.
Liakopoulou-Kyriakides, M., et al., Synergistic hydrolysis of crude corn starch by α-amylases and glucoamylases of various origins,>> *Cereal Chemistry*, 78(5): 603-607, 2001.
Medve, Jozsef et al., <<Ion-exchange chromatogaphic purification and quantitative analysis of *Trichoderma reesei* cellulases cellobiohydrolase I, II and endoglucanase II by fast protein liquid chromatography,>> Journal of Chromatography A, vol. 808, pp. 153-165, 1998.
Miller, Gail L., Use of Dinitrosalicyclic Acid Reagent for Determination of Reducing Sugar,>> Analytical Chemistry, vol. 31, pp. 426-428, 1959.
Nevalainen, K. M. Helena et al., <<The Moleclar Biology of *Trichoderma* and Its Application to the Expression of Both Homologous and Heterologous Genes,>> *Molecular Industrial Mycology*, Leong and Berka, ed., Marcel Dekker, Inc., NY, pp. 129-148, 1992.
Nunberg, Jack H. et al., <<Molecular Cloning and Characterization of the Glucoamylase Gene of *Aspergillus awamori*,>> Molecular and Cellular Biology, pp. 2306-2315, Nov. 1984.
Pearson, William R. et al., <<Improved tools for biological sequence comparison,>> Proc. Natl. Acad. Sci., U.S.A., vol. 85, pp. 2444-2448, Apr. 1988.
Penttila, Merja et al., <<A versatile transformation system for the cellulolytic filamentous fungus *Trichoderma reesei*,>> Gene, vol. 61, pp. 155-164, 1987.
Pourquie, J. et al., <<Scale Up of Cellulase Production and Utilization,>> *Biochemistry and Genetics of Cellulose Degradation*, Aubert, J. P. et al., ed., Academic Press, pp. 71-86, 1988.
Sheir-Neiss, G. et al., <<Characterization of the secreted cellulases of *Trichoderma reesei* wild type and mutants during controlled fermentations,>> Appl. Microbiol. Biotechnol., vol. 20, pp. 46-53, 1984.
Shibuya, Ichiro et al., <<Molecular Cloning of the Glucoamylase Gene of *Aspergillus shirousami* and Its Expression in *Aspergillus oryzae*,>> Agric. Biol. Chem., vol. 54, No. 8, pp. 1905-1914, 1990.
Swinkels, J. J. M., Starch Conversion Technology,>> Vvan Beynum et al. ed.,Marcel Dekker, Inc., New York, pp. 32-38, 1985.

Takahashi, Tomoko et al., <<Different Behavior towards Raw Starch of Three Forms of Glucoamylase from a *Rhizopus* Sp. ,>> J. Biochem., vol. 98, pp. 663-671, 1985.
Taylor, Pamela M. et al., <<Some Properties of a Glucoamylase Produced by the Thermophilic Fungus *Humicola lanuginosa*,>> Carbohydrate Research, vol. 61, pp. 301-308, 1978.
Tomaz, Candida T. et al., <<Studies on the chromatographic fractionation of *Trichoderma reesei* cellulases by hydrophobic interaction,>> Journal of Chromatography A, vol. 865, pp. 123-128, 1999.
Tosi, Luis Ricardo Orsini et al., <<Purification and characterization of an extracellular glycoamylase from the thermophilic fungus *Humicola grisea* var. *thermoidea*,>> Can J. Microbiol., vol. 39, pp. 846-855, 1993.
Van Tilbeurgh, Herman et al., <<Separation of endo- and exo-type cellulases using a new affinity chromatography method,>> vol. 169, No. 2, pp. 215-218, FEBS, vol. 169, No. 2, Apr. 1984.
Ward, Michael et al., <<Use of *Aspergillus* overproducing mutants, cured for integrated plasmid, to overproduce heterologous proteins,>> Appl. Microbiol. Biotechnol., vol. 39, pp. 738-743, 1993.
Wiebe, Marilyn G. et al., <<Growth-Rate-Independent Production of Recombinant Glucoamylase by *Fusarium venenatum* JeRS 325,>> Biotechnology and Bioengineering, vol. 68, No. 3, pp. 245-251, May 5, 2000.>>.
Withers, Julie M. et al., <<Optimization and Stability of Glucoamylase Production by Recombinant Strains of *Aspergillus niger* in Chemostat Culture, Biotechnology and Bioengineering, vol. 59, No. 4, pp. 407-418, Aug. 20, 1998.>>.
Whisstock et al., <<Prediction of Protein Function from Protein Sequence and Structure,>> Quarterly Reviews of Biophysics, 2003, vol. 36 No. 3, pp. 307-340.
Witkowski et al., <<Conversion of a Beta-ketoacyl Synthase to a Malonyl Decarboxylase by Replacement of the Active-site Cysteine with Glutamine,>> Biochemistry, Sep. 7, 1999, vol. 38, No. 36, pp. 11643-11650.
European Search Report for Application No. EP 06 00 9350, dated Sep. 5, 2006.
European Search Report for Application No. EP 04 81 1428, dated Sep. 7, 2007.
International Search Report and Written Opinion of the International Searching Authority for International Application No. PCT/US04/38713, dated Jul. 7, 2005.

* cited by examiner

*H. grisea* GSHE nucleotide sequence with *putative* introns bold & underlined.

ATGCATACCTTCTCCAAGCTCCTCGTCCTGGGCTCTGCCGTCCAGTCTGCCCTCGGGCGGCCTCACGGCT
CTTCGCGTCTCCAGGAACGCGCTGCCGTTGATACCTTCATCAACACCGAGAAGCCCATCGCATGGAACAA
GCTGCTCGCCAACATCGGCCCTAACGGCAAAGCCGCTCCCGGTGCCGCCGCCGGCGTTGTGATTGCCAGC
CCTTCCAGGACGGACCCTCCTT**GTACGTGGTGGCATGGAATGGACCCAAGAGACTGGTTTTAGATGAAAG
AGAGTTTCTGCTAACCGCCACACCCAG**ACTTCTTCACCTGGACCCGCGATGCCGCCCTGGTCCTCACCGG
CATCATCGAGTCCCTTGGCCACAACTACAACACCACCCTGCAGACCGTCATCCAGAACTACGTCGCGTCG
CAGGCCAAGCTGCAGCAGGTCTCGAACCCCTCGGGAACCTTCGCCGACGGCTCGGGTCTCGGTGAGGCCA
AGTTCAATGTCGACCTCACTGCCTTCACTGGCGAATGGGGTCGCCCTCAGAGGGACGGCCCGCCCCTGCG
CGCCATCGCTCTCATCCAGTACGCCAAGTGGCTGATCGCCAACGGCTACAAGAGCACGGCCAAGAGCGTC
GTCTGGCCCGTCGTCAAGAACGATCTCGCCTACACGGCCCAGTACTGGAACGAGACCGGCTTCGATCTCT
GGGAGGAGGTCCCCGGCAGCTCGTTCTTTACCATCGCCAGCTCTCACAGGG**GTGAGTCATTTATTGTTCA
GTGTTTTCTCATTGAATAATTACCGGAATGCCACTGACGCCAAACAG**CTCTGACTGAGGGTGCTTACCTC
GCCGCTCAGCTCGACACCGAGTGCCGCGCCTGCACGACCGTCGCCCCTCAGGTTCTGTGCTTCCAGCAGG
CCTTCTGGAACTCCAAGGGCAACTATGTCGTCTCCAACA**GTAAGATCCCTACACCAACAAAAAAAATCGA
AAAGGAACGTTAGCTGACCCTTCTAG**TCAACGGCGGCGAGTATCGCTCCGGCAAGGACGCCAACTCGATC
CTGGCGTCCATCCACAACTTCGACCCTGAGGCCGGCTGCGACAACCTGACCTTCCAGCCCTGCAGCGAGC
GCGCCCTGGCCAACCACAAGGCCTATGTCGACTCGTTCCGCAACCTCTACGCCATCAACAAGGGCATCGC
CCAGGGCAAGGCCGTTGCCGTCGGCCGCTACTCGGAGGATGTCTACTACAACGGCAACCCGTGGTACCTG
GCCAACTTTGCCGCCGCCGAGCAGCTCTACGACGCCATCTACGTGTGGAACAAGCAGGGCTCCATCACCG
TGACCTCGGTCTCCCTGCCCTTCTTCCGCGACCTTGTCTCGTCGGTCAGCACCGGCACCTACTCCAAGAG
CAGCTCGACCTTCACCAACATCGTCAACGCCGTCAAGGCCTACGCCGACGGCTTCATCGAGGTGGCGGCC
AAGTACACCCCGTCCAACGGCGCGCTCGCCGAGCAGTACGACCGCAACACGGGCAAGCCCGACTCGGCCG
CCGACCTGACGTGGTCGTACTCGGCCTTCCTCTCGGCCATCGACCGCCGCGCGGGTCTCGTCCCCCCGAG
CTGGCGGGCCAGCGTGGCCAAGAGCCAGCTGCCGTCCACCTGCTCGCGCATCGAGGTCGCCGGCACCTAC
GTCGCCGCCACGAGCACCTCGTTCCCGTCCAAGCAGACCCCGAACCCCTCCGCGGCGCCCTCCCCGTCCC
CCTACCCGACCGCCTGCGCGGACGCTAGCGAGGTGTACGTCACCTTCAACGAGCGCGTGTCGACCGCGTG
GGGCGAGACCATCAAGGTGGTGGGCAACGTGCCGGCGCTGGGGAACTGGGACACGTCCAAGGCGGTGACC
CTGTCGGCCAGCGGGTACAAGTCGAATGATCCCCTCTGGAGCATCACGGTGCCCATCAAGGCGACGGGCT
CGGCCGTGCAGTACAAGTATATCAAGGTCGGCACCAACGGGAAGATTACTTGGGAGTCGGACCCCAACAG
GAGCATTACCCTGCAGACGGCGTCGTCTGCGGGCAAGTGCGCCGCGCAGACGGTGAATGATTCGTGGCGT
TAA

FIG. 1

*H. grisea* GSHE protein sequence with *putative* signal sequence underlined.

*H. grisea* Mature GSHE protein sequence

```
AAGCTTACTAGTACTTCTCGAGCTCTGTACATGTCCGGTCGCGACGTACGCGTATCGATGGCGCCAGC
TGCAGGCGGCCGCCTGCAGCCACTTGCAGTCCCGTGGAATTCTCACGGTGAATGTAGGCCTTTTGTAG
GGTAGGAATTGTCACTCAAGCACCCCCAACCTCCATTACGCCTCCCCCATAGAGTTCCCAATCAGTGA
GTCATGGCACTGTTCTCAAATAGATTGGGGAGAAGTTGACTTCCGCCCAGAGCTGAAGGTCGCACAAC
CGCATGATATAGGGTCGGCAACGGCAAAAAAGCACGTGGCTCACCGAAAAGCAAGATGTTTGCGATCT
AACATCCAGGAACCTGGATACATCCATCATCACGCACGACCACTTTGATCTGCTGGTAAACTCGTATT
CGCCCTAAACCGAAGTGCGTGGTAAATCTACACGTGGGCCCCTTTCGGTATACTGCGTGTGTCTTCTC
TAGGTGCCATTCTTTTCCCTTCCTCTAGTGTTGAATTGTTTGTGTTGGAGTCCGAGCTGTAACTACCT
CTGAATCTCTGGAGAATGGTGGACTAACGACTACCGTGCACCTGCATCATGTATATAATAGTGATCCT
GAGAAGGGGGGTTTGGAGCAATGTGGGACTTTGATGGTCATCAAACAAAGAACGAAGACGCCTCTTTT
GCAAAGTTTTGTTTCGGCTACGGTGAAGAACTGGATACTTGTTGTGTCTTCTGTGTATTTTTGTGGCA
ACAAGAGGCCAGAGACAATCTATTCAAACACCAAGCTTGCTCTTTTGAGCTACAAGAACCTGTGGGT
ATATATCTAGAGTTGTGAAGTCGGTAATCCCGCTGTATAGTAATACGAGTCGCATCTAAATACTCCGA
AGCTGCTGCGAACCCGGAGAATCGAGATGTGCTGGAAAGCTTCTAGCGAGCGGCTAAATTAGCATGAA
AGGCTATGAGAAATTCTGGAGACGGCTTGTTGAATCATGGCGTTCCATTCTTCGACAAGCAAAGCGTT
CCGTCGCAGTAGCAGGCACTCATTCCCGAAAAAACTCGGAGATTCCTAAGTAGCGATGGAACCGGAAT
AATATAATAGGCAATACATTGAGTTGCCTCGACGGTTGCAATGCAGGGGTACTGAGCTTGGACATAAC
TGTTCCGTACCCCACCTCTTCTCAACCTTTGGCGTTTCCCTGATTCAGCGTACCCGTACAAGTCGTAA
TCACTATTAACCCAGACTGACCGGACGTGTTTTGCCCTTCATTTGGAGAAATAATGTCATTGCGATGT
GTAATTTGCCTGCTTGACCGACTGGGGCTGTTCGAAGCCCGAATGTAGGATTGTTATCCGAACTCTGC
TCGTAGAGGCATGTTGTGAATCTGTGTCGGGCAGGACACGCCTCGAAGGTTCACGGCAAGGGAAACCA
CCGATAGCAGTGTCTAGTAGCAACCTGTAAAGCCGCAATGCAGCATCACTGGAAAATACAAACCAATG
GCTAAAAGTACATAAGTTAATGCCTAAAGAAGTCATATACCAGCGGCTAATAATTGTACAATCAAGTG
GCTAAACGTACCGTAATTTGCCAACGGCTTGTGGGGTTGCAGAAGCAACGGCAAAGCCCCACTTCCCC
ACGTTTGTTTCTTCACTCAGTCCAATCTCAGCTGGTGATCCCCCAATTGGGTCGCTTGTTTGTTCCGG
TGAAGTGAAAGAAGACAGAGGTAAGAATGTCTGACTCGGAGCGTTTTGCATACAACCAAGGGCAGTGA
TGGAAGACAGTGAAATGTTGACATTCAAGGAGTATTTAGCCAGGGATGCTTGAGTGTATCGTGTAAGG
AGGTTTGTCTGCCGATACGACGAATACTGTATAGTCACTTCTGATGAAGTGGTCCATATTGAAATGTA
AAGTCGGCACTGAACAGGCAAAAGATTGAGTTGAAACTGCCTAAGATCTCGGGCCCTCGGGCCTTCGG
CCTTTGGGTGTACATGTTTGTGCTCCGGGCAAATGCAAGTGTGGTAGGATCGAACACACTGCTGCCT
TTACCAAGCAGCTGAGGGTATGTGATAGGCAAATGTTCAGGGGCCACTGCATGGTTTCGAATAGAAAG
AGAAGCTTAGCCAAGAACAATAGCCGATAAAGATAGCCTCATTAAACGGAATGAGCTAGTAG
```

FIG. 4A

```
GCAAAGTCAGCGAATGTGTATATATAAAGGTTCGAGGTCCGTGCCTCCCTCATGCTCTCCCCATCTAC
TCATCAACTCAGATCCTCCAGGAGACTTGTACACCATCTTTTGAGGCACAGAAACCCAATAGTCAACC
ATCACAAGTTTGTACAAAAAAGCAGGCTCCGCGGCCGCCCCCTTCAACATGCATACCTTCTCCAAGCT
CCTCGTCCTGGGCTCTGCCGTCCAGTCTGCCCTCGGGCGGCCTCACGGCTCTTCGCGTCTCCAGGAAC
GCGCTGCCGTTGATACCTTCATCAACACCGAGAAGCCCATCGCATGGAACAAGCTGCTCGCCAACATC
GGCCCTAACGGCAAAGCCGCTCCCGGTGCCGCCGCCGGCGTTGTGATTGCCAGCCCTTCCAGGACGGA
CCCTCCTTGTACGTGGTGGCATGGAATGGACCCAAGAGACTGGTTTTAGATGAAAGAGAGTTTCTGCT
AACCGCCACACCCAGACTTCTTCACCTGGACCCGCGATGCCGCCCTGGTCCTCACCGGCATCATCGAG
TCCCTTGGCCACAACTACAACACCACCCTGCAGACCGTCATCCAGAACTACGTCGCGTCGCAGGCCAA
GCTGCAGCAGGTCTCGAACCCCTCGGGAACCTTCGCCGACGGCTCGGGTCTCGGTGAGGCCAAGTTCA
ATGTCGACCTCACTGCCTTCACTGGCGAATGGGGTCGCCCTCAGAGGGACGGCCCGCCCCTGCGCGCC
ATCGCTCTCATCCAGTACGCCAAGTGGCTGATCGCCAACGGCTACAAGAGCACGGCCAAGAGCGTCGT
CTGGCCCGTCGTCAAGAACGATCTCGCCTACACGGCCCAGTACTGGAACGAGACCGGCTTCGATCTCT
GGGAGGAGGTCCCCGGCAGCTCGTTCTTTACCATCGCAGCTCTCACAGGGGTGAGTCATTTATTGTT
CAGTGTTTTCTCATTGAATAATTACCGGAATGCCACTGACGCCAAACAGCTCTGACTGAGGGTGCTTA
CCTCGCCGCTCAGCTCGACACCGAGTGCCGCGCCTGCACGACCGTCGCCCCTCAGGTTCTGTGCTTCC
AGCAGGCCTTCTGGAACTCCAAGGGCAACTATGTCGTCTCCAACAGTAAGATCCCTACACCAACAAAA
AAAATCGAAAAGGAACGTTAGCTGACCCTTCTAGTCAACGGCGGCGAGTATCGCTCCGGCAAGGACGC
CAACTCGATCCTGGCGTCCATCCACAACTTCGACCCTGAGGCCGGCTGCGACAACCTGACCTTCCAGC
CCTGCAGCGAGCGCGCCCTGGCCAACCACAAGGCCTATGTCGACTCGTTCCGCAACCTCTACGCCATC
AACAAGGGCATCGCCCAGGGCAAGGCCGTTGCCGTCGGCCGCTACTCGGAGGATGTCTACTACAACGG
CAACCCGTGGTACCTGGCCAACTTTGCCGCCGCCGAGCAGCTCTACGACGCCATCTACGTGTGGAACA
AGCAGGGCTCCATCACCGTGACCTCGGTCTCCCTGCCCTTCTTCCGCGACCTTGTCTCGTCGGTCAGC
ACCGGCACCTACTCCAAGAGCAGCTCGACCTTCACCAACATCGTCAACGCCGTCAAGGCCTACGCCGA
CGGCTTCATCGAGGTGGCGGCCAAGTACACCCCGTCCAACGGCGCGCTCGCCGAGCAGTACGACCGCA
ACACGGGCAAGCCCGACTCGGCCGCCGACCTGACGTGGTCGTACTCGGCCTTCCTCTCGGCCATCGAC
CGCCGCGGGTCTCGTCCCCCCGAGCTGGCGGGCCAGCGTGGCCAAGAGCCAGCTGCCGTCCACCTG
CTCGCGCATCGAGGTCGCCGGCACCTACGTCGCCGCCACGAGCACCTCGTTCCCGTCCAAGCAGACCC
CGAACCCCTCCGCGGCGCCCTCCCCGTCCCCTACCCGACCGCCTGCGCGGACGCTAGCGAGGTGTAC
GTCACCTTCAACGAGCGCGTGTCGACCGCGTGGGGCGAGACCATCAAGGTGGTGGGCAACGTGCCGGC
GCTGGGGAACTGGGACACGTCCAAGGCGGTGACCCTGTCGGCCAGCGGGTACAAGTCGAATGATCCCC
TCTGGAGCATCACGGTGCCCATCAAGGCGACGGGCTCGGCCGTGCAGTACAAGTATATCAAG
```

FIG. 4B

```
GTCGGCACCAACGGGAAGATTACTTGGGAGTCGGACCCCAACAGGAGCATTACCCTGCAGACGGCGTCGT
CTGCGGGCAAGTGCGCCGCGCAGACGGTGAATGATTCGTGGCGTTAAAAGGGTGGGCGCGCCGACCCA
GCTTTCTTGTACAAAGTGGTGATCGCGCCAGCTCCGTGCGAAAGCCTGACGCACCGGTAGATTCTTGG
TGAGCCCGTATCATGACGGCGGCGGGAGCTACATGGCCCCGGGTGATTTATTTTTTTTGTATCTACTT
CTGACCCTTTTCAAATATACGGTCAACTCATCTTTCACTGGAGATGCGGCCTGCTTGGTATTGCGATG
TTGTCAGCTTGGCAAATTGTGGCTTTCGAAAACACAAAACGATTCCTTAGTAGCCATGCATTTTAAGA
TAACGGAATAGAAGAAAGAGGAAATTAAAAAAAAAAAAAAAACAAACATCCCGTTCATAACCCGTAGA
ATCGCCGCTCTTCGTGTATCCCAGTACCAGTTTATTTTGAATAGCTCGCCCGCTGGAGAGCATCCTGA
ATGCAAGTAACAACCGTAGAGGCTGACACGGCAGGTGTTGCTAGGGAGCGTCGTGTTCTACAAGGCCA
GACGTCTTCGCGGTTGATATATATGTATGTTTGACTGCAGGCTGCTCAGCGACGACAGTCAAGTTCGC
CCTCGCTGCTTGTGCAATAATCGCAGTGGGGAAGCCACACCGTGACTCCCATCTTTCAGTAAAGCTCT
GTTGGTGTTTATCAGCAATACACGTAATTTAAACTCGTTAGCATGGGGCTGATAGCTTAATTACCGTT
TACCAGTGCCATGGTTCTGCAGCTTTCCTTGGCCCGTAAAATTCGGCGAAGCCAGCCAATCACCAGCT
AGGCACCAGCTAAACCCTATAATTAGTCTCTTATCAACACCATCCGCTCCCCCGGGATCAATGAGGAG
AATGAGGGGGATGCGGGCTAAAGAAGCCTACATAACCCTCATGCCAACTCCCAGTTTACACTCGTCG
AGCCAACATCCTGACTATAAGCTAACACAGAATGCCTCAATCCTGGGAAGAACTGGCCGCTGATAAGC
GCGCCCGCCTCGCAAAAACCATCCCTGATGAATGGAAAGTCCAGACGCTGCCTGCGGAAGACAGCGTT
ATTGATTTCCCAAAGAAATCGGGGATCCTTTCAGAGGCCGAACTGAAGATCACAGAGGCCTCCGCTGC
AGATCTTGTGTCCAAGCTGGCGGCCGGAGAGTTGACCTCGGTGGAAGTTACGCTAGCATTCTGTAAAC
GGGCAGCAATCGCCCAGCAGTTAGTAGGGTCCCCTCTACCTCTCAGGGAGATGTAACAACGCCACCTT
ATGGGACTATCAAGCTGACGCTGGCTTCTGTGCAGACAAACTGCGCCCACGAGTTCTTCCCTGACGCC
GCTCTCGCGCAGGCAAGGGAACTCGATGAATACTACGCAAAGCACAAGAGACCCGTTGGTCCACTCCA
TGGCCTCCCCATCTCTCTCAAAGACCAGCTTCGAGTCAAGGTACACCGTTGCCCCTAAGTCGTTAGAT
GTCCCTTTTTGTCAGCTAACATATGCCACCAGGGCTACGAAACATCAATGGGCTACATCTCATGGCTA
AACAAGTACGACGAAGGGGACTCGGTTCTGACAACCATGCTCCGCAAAGCCGGTGCCGTCTTCTACGT
CAAGACCTCTGTCCCGCAGACCCTGATGGTCTGCGAGACAGTCAACAACATCATCGGGCGCACCGTCA
ACCCACGCAACAAGAACTGGTCGTGCGGCGGCAGTTCTGGTGGTGAGGGTGCGATCGTTGGGATTCGc
RVTGGTGGCGTCATCGGTGTAGGAACGGATATCGGTGGCTCGATTCGAGTGCCGGCCGCGTTCAACTT
CCTGTACGGTCTAAGGCCGAGTCATGGGCGGCTGCCGTATGCAAAGATGGCGAACAGCATGGAGGGTC
AGGAGACGGTGCACAGCGTTGTCGGGCCGATTACGCACTCTGTTGAGGGTGAGTCCTTCGCCTCTTCC
TTCTTTTCCTGCTCTATACCAGGCCTCCACTGTCCTCCTTTCTTGCTTTTTATACTATATACGAGACC
GGCAGTCACTGATGAAGTATGTTAGACCTCCGCCTCTTCACCAAATCCGTCCTCGGTCAG
```

*FIG. 4C*

```
GAGCCATGGAAATACGACTCCAAGGTCATCCCCATGCCCTGGCGCCAGTCCGAGTCGGACATTATTGCCT
CCAAGATCAAGAACGGCGGGCTCAATATCGGCTACTACAACTTCGACGGCAATGTCCTTCCACACCCT
CCTATCCTGCGCGGCGTGGAAACCACCGTCGCCGCACTCGCCAAAGCCGGTCACACCGTGACCCCGTG
GACGCCATACAAGCACGATTTCGGCCACGATCTCATCTCCCATATCTACGCGGCTGACGGCAGCcRVG
CCGACGTAATGCGCGATATCAGTGCATCCGGCGAGCCGGCGATTCCAAATATCAAAGACCTACTGAAC
CCGAACATCAAAGCTGTTAACATGAACGAGCTCTGGGACACGCATCTCCAGAAGTGGAATTACCAGAT
GGAGTACCTTGAGAAATGGCGGGAGGCTGAAGAAAAGGCCGGGAAGGAACTGGACGCCATCATCGCGC
CGATTACGCCTACCGCTGCGGTACGGCATGACCAGTTCCGGTACTATGGGTATGCCTCTGTGATCAAC
CTGCTGGATTTCACGAGCGTGGTTGTTCCGGTTACCTTTGCGGATAAGAACATCGATAAGAAGAATGA
GAGTTTCAAGGCGGTTAGTGAGCTTGATGCCCTCGTGCAGGAAGAGTATGATCCGGAGGCGTACCATG
GGGCACCGGTTGCAGTGCAGGTTATCGGACGGAGACTCAGTGAAGAGAGGACGTTGGCGATTGCAGAG
GAAGTGGGGAAGTTGCTGGGAAATGTGGTGACTCCATAGCTAATAAGTGTCAGATAGCAATTTGCACA
AGAAATCAATACCAGCAACTGTAAATAAGCGCTGAAGTGACCATGCCATGCTACGAAAGAGCAGAAAA
AAACCTGCCGTAGAACCGAAGAGATATGACACGCTTCCATCTCTCAAAGGAAGAATCCCTTCAGGGTT
GCGTTTCCAGTCTAGACACGTATAACGGCACAAGTGTCTCTCACCAAATGGGTTATATCTCAAATGTG
ATCTAAGGATGGAAAGCCCAGAATATCGATCGCGCGCAGATCCATATATAGGGCCCGGGTTATAATTA
CCTCAGGTCGACGTCCCATGGCCATTCGAATTCGTAATCATGGTCATAGCTGTTTCCTGTGTGAAATT
GTTATCCGCTCACAATTCCACACAACATACGAGCCGGAAGCATAAAGTGTAAAGCCTGGGGTGCCTAA
TGAGTGAGCTAACTCACATTAATTGCGTTGCGCTCACTGCCCGCTTTCCAGTCGGGAAACCTGTCGTG
CCAGCTGCATTAATGAATCGGCCAACGCGCGGGAGAGGCGGTTTGCGTATTGGGCGCTCTTCCGCTT
CCTCGCTCACTGACTCGCTGCGCTCGGTCGTTCGGCTGCGGCGAGCGGTATCAGCTCACTCAAAGGCG
GTAATACGGTTATCCACAGAATCAGGGGATAACGCAGGAAAGAACATGTGAGCAAAAGGCCAGCAAAA
GGCCAGGAACCGTAAAAAGGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAAAGATACCAGGCGTTTCCC
CCTGGAAGCTCCCTCGTGCGCTCTCCTGTTCCGACCCTGCCGCTTACCGGATACCTGTCCGCCTTTCT
CCCTTCGGGAAGCGTGGCGCTTTCTCATAGCTCACGCTGTAGGTATCTCAGTTCGGTGTAGGTCGTTC
GCTCCAAGCTGGGCTGTGTGCACGAACCCCCGTTCAGCCCGACCGCTGCGCCTTATCCGGTAACTAT
CGTCTTGAGTCCAACCCGGTAAGACACGACTTATCGCCACTGGCAGCAGCCACTGGTAACAGGATTAG
CAGAGCGAGGTATGTAGGCGGTGCTACAGAGTTCTTGAAGTGGTGGCCTAACTACGGCTACACTAGAA
GAACAGTATTTGGTATCTGCGCTCTGCTGAAGCCAGTTACCTTCGGAAAAAGAGTTGGTAGCTCTTGA
TCCGGCAAACAAACCACCGCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTCAGTGGAACGA
```

FIG. 4D

```
AAACTCACGTTAAGGGATTTTGGTCATGAGATTATCAAAAAGGATCTTCACCTAGATCCTTTTAAATT
AAAAATGAAGTTTTAAATCAATCTAAAGTATATATGAGTAAACTTGGTCTGACAGTTACCAATGCTTA
ATCAGTGAGGCACCTATCTCAGCGATCTGTCTATTTCGTTCATCCATAGTTGCCTGACTCCCCGTCGT
GTAGATAACTACGATACGGGAGGGCTTACCATCTGGCCCCAGTGCTGCAATGATACCGCGAGACCCAC
GCTCACCGGCTCCAGATTTATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAGAGTAAGTAGTTCGCCAGT
TAATAGTTTGCGCAACGTTGTTGCCATTGCTACAGGCATCGTGGTGTCACGCTCGTCGTTTGGTATGG
CTTCATTCAGCTCCGGTTCCCAACGATCAAGGCGAGTTACATGATCCCCCATGTTGTGCAAAAAAGCG
GTTAGCTCCTTCGGTCCTCCGATCGTTGTCAGAAGTAAGTTGGCCGCAGTGTTATCACTCATGGTTAT
GGCAGCACTGCATAATTCTCTTACTGTCATGCCATCCGTAAGATGCTTTTCTGTGACTGGTGAGTACT
CAACCAAGTCATTCTGAGAATAGTGTATGCGGCGACCGAGTTGCTCTTGCCCGGCGTCAATACGGGAT
AATACCGCGCCACATAGCAGAACTTTAAAAGTGCTCATCATTGGAAAACGTTCTTCGGGGCGAAAACT
CTCAAGGATCTTACCGCTGTTGAGATCCAGTTCGATGTAACCCACTCGTGCACCCAACTGATCTTCAG
CATCTTTTACTTTCACCAGCGTTTCTGGGTGAGCAAAAACAGGAAGGCAAAATGCCGCAAAAAAGGGA
ATAAGGGCGACACGGAAATGTTGAATACTCATACTCTTCCTTTTTCAATATTATTGAAGCATTTATCA
GGGTTATTGTCTCATGAGCGGATACATATTTGAATGTATTTAGAAAAATAAACAAATAGGGGTTCCGC
GCACATTTCCCCGAAAAGTGCCACCTGACGTCTAAGAAACCATTATTATCATGACATTAACCTATAAA
AATAGGCGTATCACGAGGCCCTTTCGTCTCGCGCGTTTCGGTGATGACGGTGAAAACCTCTGACACAT
GCAGCTCCCGGAGACGGTCACAGCTTGTCTGTAAGCGGATGCCGGGAGCAGACAAGCCCGTCAGGGCG
CGTCAGCGGGTGTTGGCGGGTGTCGGGGCTGGCTTAACTATGCGGCATCAGAGCAGATTGTACTGAGA
GTGCACCATAAAATTGTAAACGTTAATATTTTGTTAAAATTCGCGTTAAATTTTGTTAAATCAGCTC
ATTTTTTAACCAATAGGCCGAAATCGGCAAAATCCCTTATAAATCAAAAGAATAGCCCGAGATAGGGT
TGAGTGTTGTTCCAGTTTGGAACAAGAGTCCACTATTAAAGAACGTGGACTCCAACGTCAAAGGGCGA
AAAACCGTCTATCAGGGCGATGGCCCACTACGTGAACCATCACCCAAATCAAGTTTTTTGGGGTCGAG
GTGCCGTAAAGCACTAAATCGGAACCCTAAAGGGAGCCCCCGATTTAGAGCTTGACGGGGAAAGCCGG
CGAACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTACTATGGTTG
CTTTGACGTATGCGGTGTGAAATACCGCACAGATGCGTAAGGAGAAAATACCGCATCAGGCGCCATTC
GCCATTCAGGCTGCGCAACTGTTGGGAAGGGCGATCGGTGCGGGCCTCTTCGCTATTACGCCAGCTGG
CGAAAGGGGGATGTGCTGCAAGGCGATTAAGTTGGGTAACGCCAGGGTTTTCCCAGTCACGACGTTGT
AAAACGACGGCCAGTGCCC
```

FIG. 4E

Genomic Nucleotide Sequence of *Aspergillus kawachi* GSHE

```
ATGTCGTTCCGATCTCTTCTCGCCCTGAGCGGCCTTGTCTGCTCGGGGTTGGCAAGTGTGAT
TTCCAAGCGCGCGACCTTGGATTCGTGGTTGAGCAACGAAGCGACCGTGGCCCGTACTGCGA
TCCTGAATAACATCGGGGCGGACGGTGCTTGGGTGTCGGGCGCGGACTCTGGCATTGTCGTT
GCCAGTCCCAGCACCGATAACCCGGACTGTATGTTTTGAGTTCGGATTATGAATGTGTCTTG
GTTGATTGATGCTGACTGGCGTGTCTTTTGATGATTGTAGACTTCTACACCTGGACTCGCGA
CTCTGGTCTCGTCATCAAGACCCTCGTCGACCTCTTCCGCAATGGAGATACTGATCTCCTTT
CCACCATTGAGCACTACATCTCCTCTCAGGCAATTATTCAGGGTGTCAGTAACCCCTCTGGT
GATCTGTCCAGCGGTGGTCTTGGTGAGCCCAAGTTCAATGTCGATGAGACTGCCTACACCGG
TTCTTGGGGACGGCCGCAGCGTGATGGTCCTGCCCTGAGAGCAACTGCTATGATCGGCTTTG
GGCAGTGGCTGCTTGTATGTTCTCCACCTCCTTGCGTCTGATCTGCAACATATGTAGCCGAC
TGGTCAGGACAATGGCTACACCAGCGCTGCAACAGAGATTGTTTGGCCCCTCGTTAGGAACG
ACCTGTCGTATGTGGCTCAGTACTGGAACCAGACGGGATATGGTGTGTTTGATTGATCGGGG
TTCAAGGGTGTTTGTGCATCGGAGCTAACTTCGCGGTCGCAGATCTCTGGGAAGAAGTTAAT
GGCTCGTCCTTCTTCACTATTGCCGTGCAACACCGCGCCCTCGTCGAAGGTAGTGCCTTCGC
GACGGCCGTCGGCTCGTCCTGCTCCTGGTGTGATTCGCAGGCACCTCAGATTCTCTGTTACT
TGCAGTCCTTCTGGACCGGCAGCTACATCCTGGCCAACTTTGACAGCAGCCGTTCCGGCAAG
GACACAAACACCCTCCTGGGAAGCATCCACACCTTTGATCCTGAGGCTGGATGCGACGACTC
CACCTTCCAGCCCTGCTCCCGCGTGCGCTCGCCAACCATAAGGAGGTTGTAGACTCTTTCC
GCTCGATCTATACTCTCAACGATGGTCTCAGTGACAGTGAGGCGGTTGCGGTCGGTCGGTAC
CCTGAGGATAGCTACTACAACGGCAACCCGTGGTTCCTGTGCACCTTGGCTGCCGCGGAACA
GCTGTACGATGCTCTGTACCAGTGGGACAAGCAGGGGTCGTTGGAGATCACAGACGTGTCAC
TTGACTTCTTCAAGGCTCTGTACAGTGGTGCTGCCACCGGCACGTACTCTTCGTCCAGCTCG
ACCTATAGCAGCATTGTGAGTGCCGTCAAGACTTTCGCTGATGGTTTTGTTTCTATTGTGGT
AAGTCTACGCTAGACGAGCGCTCATATTTACAGAGGGTGCGTACTAACAGGATTAGGAAACT
CACGCCGCAAGCAACGGCTCTCTGTCTGAGCAATTCGACAAGTCTGATGGCGACGAGCTTTC
TGCTCGCGATCTGACCTGGTCTTACGCTGCTCTGCTGACCGCCAACAACCGTCGTAATTCTG
TCGTGCCCCGTCTTGGGGTGAGACCTCTGCCAGCAGCGTGCCCGGCACCTGTGCGGCTACC
TCTGCCTCTGGTACCTACAGCAGTGTGACCGTCACCTCGTGGCCGAGCATCGTGGCTACTGG
TGGCACCACTACGACGGCTACTACCACTGGATCGGGCGGCGTGACCTCGACCAGCAAGACCA
CCACAACTGCTAGTAAGACCAGCACCACTACGTCCTCGACCTCCTGCACCACCCCCACTGCC
GTAGCTGTGACCTTTGATCTGACGGCGACCACCACCTACGGCGAGAACATCTACCTGGTCGG
GTCGATCTCTCAGCTCGGTGACTGGGAGACCAGCGATGGCATAGCTCTGAGCGCTGACAAGT
ACACTTCCAGCAACCCGCTTTGGTATGTAACTGTGACTCTGCCGGCTGGTGAGTCATTTGAG
TACAAGTTCATCCGCGTCGAGAGCGATGACTCCGTGGAGTGGGAGAGCGACCCGAACCGGGA
ATACACCGTTCCTCAGGCGTGCGGCGAGTCGACCGCGACGGTGACCGACACCTGGCGGTAG
```

*FIG. 6*

*Aspergillus awamori* var. *kawachi* GSHE precursor
(i.e.: with signal sequence underlined) protein sequence.

Mature (i.e. expressed protein with the putative signal sequence removed)
*Aspergillus awamori* var. *kawachi* GSHE protein sequence.

ATLDSWLSNEATVARTAILNNIGADGAWVSGADSGIVVASPSTDNPDYFYTWTRDSGLVIKT
LVDLFRNGDTDLLSTIEHYISSQAIIQGVSNPSGDLSSGGLGEPKFNVDETAYTGSWGRPQR
DGPALRATAMIGFGQWLLDNGYTSAATEIVWPLVRNDLSYVAQYWNQTGYDLWEEVNGSSFF
TIAVQHRALVEGSAFATAVGSSCSWCDSQAPQILCYLQSFWTGSYILANFDSSRSGKDTNTL
LGSIHTFDPEAGCDDSTFQPCSPRALANHKEVVDSFRSIYTLNDGLSDSEAVAVGRYPEDSY
YNGNPWFLCTLAAAEQLYDALYQWDKQGSLEITDVSLDFFKALYSGAATGTYSSSSSTYSSI
VSAVKTFADGFVSIVETHAASNGSLSEQFDKSDGDELSARDLTWSYAALLTANNRRNSVVPP
SWGETSASSVPGTCAATSASGTYSSVTVTSWPSIVATGGTTTTATTTGSGGVTSTSKTTTTA
SKTSTTTSSTSCTTPTAVAVTFDLTATTTYGENIYLVGSISQLGDWETSDGIALSADKYTSS
NPLWYVTVTLPAGESFEYKFIRVESDDSVEWESDPNREYTVPQACGESTATVTDTWR

*FIG. 7B*

```
SEQUENCE LISTING

<160> NUMBER OF SEQ ID NOS: 11

<210> SEQ ID NO 1
<211> LENGTH: 2103
<212> TYPE: DNA
<213> ORGANISM: Humicola grisea var. thermoidea

<400> SEQUENCE: 1 atgcataect tctccaaget cctcgtcctg ggctctgccg tccagtctgc cctcgggcgg       60
cctcacggct cttcgcgtct ccaggaacgc gctgccgttg ataccttcat caacaccgag      120
aagcccatcg catggaacaa gctgctcgcc aacatcggcc ctaacggcaa agccgctccc      180
ggtgccgccg ccggcgttgt gattgccagc ccttccagga cggaccctcc ttgtacgtgg      240
tggcatggaa tggacccaag agactggttt tagatgaaag agagtttctg ctaaccgcca      300
cacccagact tcttcacctg gacccgcgat gccgccctgg tcctcaccgg catcatcgag      360
tcccttggcc acaactacaa caccaccctg cagaccgtca tccagaacta cgtcgcgtcg      420
```

```
caggccaagc tgcagcaggt ctcgaacccc tcgggaacct tcgccgacgg ctcgggtctc      480
ggtgaggcca agttcaatgt cgacctcact gccttcactg gcgaatgggg tcgccctcag      540
agggacggcc cgcccctgcg cgccatcgct ctcatccagt acgccaagtg gctgatcgcc      600
aacggctaca gagcacggc caagagcgtc gtctggcccg tcgtcaagaa cgatctcgcc       660
tacacggccc agtactggaa cgagaccggc ttcgatctct gggaggaggt ccccggcagc      720
tcgttcttta ccatcgccag ctctcacagg ggtgagtcat ttattgttca gtgttttctc      780
attgaataat taccggaatg ccactgacgc caaacagctc tgactgaggg tgcttacctc      840
gccgctcagc tcgacaccga gtgccgcgcc tgcacgaccg tcgcccctca ggttctgtgc      900
ttccagcagg ccttctggaa ctccaagggc aactatgtcg tctccaacag taagatccct      960
acaccaacaa aaaaaatcga aaggaacgt tagctgaccc ttctagtcaa cggcggcgag      1020
tatcgctccg gcaaggacgc caactcgatc ctggcgtcca tccacaactt cgaccctgag     1080
gccggctgcg acaacctgac cttccagccc tgcagcgagc gcgccctggc caaccacaag     1140
gcctatgtcg actcgttccg caacctctac gccatcaaca agggcatcgc ccagggcaag     1200
gccgttgccg tcggccgcta ctcggaggat gtctactaca cggcaaccc gtggtacctg      1260 gccaactttg ccgccgccga gcagctctac gacgccatct acgtgtggaa caagcagggc     1320
tccatcaccg tgacctcggt ctccctgccc ttcttccgcg accttgtctc gtcggtcagc     1380
accggcacct actccaagag cagctcgacc ttcaccaaca tcgtcaacgc cgtcaaggcc     1440
tacgccgacg gcttcatcga ggtggcggcc aagtacaccc cgtccaacgg cgcgctcgcc     1500
gagcagtacg accgcaacac gggcaagccc gactcggccg ccgacctgac gtggtcgtac     1560
tcggccttcc tctcggccat cgaccgccgc gcgggtctcg tcccccgag ctggcgggcc      1620 agcgtggcca agagccagct gccgtccacc tgctcgcgca tcgaggtcgc cggcacctac     1680
gtcgccgcca cgagcacctc gttcccgtcc aagcagaccc cgaacccctc cgcggcgccc     1740
tccccgtccc cctacccgac cgcctgcgcg gacgctagcg aggtgtacgt caccttcaac     1800
gagcgcgtgt cgaccgcgtg gggcgagacc atcaaggtgg tgggcaacgt gccggcgctg     1860
gggaactggg acacgtccaa ggcggtgacc ctgtcggcca gcgggtacaa gtcgaatgat     1920
cccctctgga gcatcacggt gcccatcaag gcgacgggct cggccgtgca gtacaagtat     1980
atcaaggtcg gcaccaacgg gaagattact tgggagtcgg accccaacag gagcattacc     2040
ctgcagacgg cgtcgtctgc gggcaagtgc gccgcgcaga cggtgaatga ttcgtggcgt     2100
taa                                                                  2103
```

<210> SEQ ID NO 2
<211> LENGTH: 634
<212> TYPE: PRT
<213> ORGANISM: Humicola grisea var. thermoidea

<400> SEQUENCE: 2

Met His Thr Phe Ser Lys Leu Leu Val Leu Gly Ser Ala Val Gln Ser
1               5                   10                  15

Ala Leu Gly Arg Pro His Gly Ser Ser Arg Leu Gln Glu Arg Ala Ala
            20                  25                  30

Val Asp Thr Phe Ile Asn Thr Glu Lys Pro Ile Ala Trp Asn Lys Leu
        35                  40                  45

Leu Ala Asn Ile Gly Pro Asn Gly Lys Ala Ala Pro Gly Ala Ala Ala
    50                  55                  60

```
Gly Val Val Ile Ala Ser Pro Ser Arg Thr Asp Pro Pro Tyr Phe Phe
 65                  70                  75                  80

Thr Trp Thr Arg Asp Ala Ala Leu Val Leu Thr Gly Ile Ile Glu Ser
                 85                  90                  95

Leu Gly His Asn Tyr Asn Thr Thr Leu Gln Thr Val Ile Gln Asn Tyr
            100                 105                 110

Val Ala Ser Gln Ala Lys Leu Gln Gln Val Ser Asn Pro Ser Gly Thr
        115                 120                 125

Phe Ala Asp Gly Ser Gly Leu Gly Glu Ala Lys Phe Asn Val Asp Leu
    130                 135                 140

Thr Ala Phe Thr Gly Glu Trp Gly Arg Pro Gln Arg Asp Gly Pro Pro
145                 150                 155                 160

Leu Arg Ala Ile Ala Leu Ile Gln Tyr Ala Lys Trp Leu Ile Ala Asn
                165                 170                 175

Gly Tyr Lys Ser Thr Ala Lys Ser Val Val Trp Pro Val Val Lys Asn
            180                 185                 190

Asp Leu Ala Tyr Thr Ala Gln Tyr Trp Asn Glu Thr Gly Phe Asp Leu
        195                 200                 205

Trp Glu Glu Val Pro Gly Ser Ser Phe Phe Thr Ile Ala Ser Ser His
    210                 215                 220

Arg Ala Leu Thr Glu Gly Ala Tyr Leu Ala Ala Gln Leu Asp Thr Glu
225                 230                 235                 240

Cys Arg Ala Cys Thr Thr Val Ala Pro Gln Val Leu Cys Phe Gln Gln
                245                 250                 255

Ala Phe Trp Asn Ser Lys Gly Asn Tyr Val Val Ser Asn Ile Asn Gly
            260                 265                 270

Gly Glu Tyr Arg Ser Gly Lys Asp Ala Asn Ser Ile Leu Ala Ser Ile
        275                 280                 285

His Asn Phe Asp Pro Glu Ala Gly Cys Asp Asn Leu Thr Phe Gln Pro
    290                 295                 300

Cys Ser Glu Arg Ala Leu Ala Asn His Lys Ala Tyr Val Asp Ser Phe
305                 310                 315                 320

Arg Asn Leu Tyr Ala Ile Asn Lys Gly Ile Ala Gln Gly Lys Ala Val
                325                 330                 335

Ala Val Gly Arg Tyr Ser Glu Asp Val Tyr Tyr Asn Gly Asn Pro Trp
            340                 345                 350

Tyr Leu Ala Asn Phe Ala Ala Glu Gln Leu Tyr Asp Ala Ile Tyr
        355                 360                 365

Val Trp Asn Lys Gln Gly Ser Ile Thr Val Thr Ser Val Ser Leu Pro
370                 375                 380

Phe Phe Arg Asp Leu Val Ser Ser Val Ser Thr Gly Thr Tyr Ser Lys
385                 390                 395                 400

Ser Ser Ser Thr Phe Thr Asn Ile Val Asn Ala Val Lys Ala Tyr Ala
            405                 410                 415

Asp Gly Phe Ile Glu Val Ala Ala Lys Tyr Thr Pro Ser Asn Gly Ala
        420                 425                 430

Leu Ala Glu Gln Tyr Asp Arg Asn Thr Gly Lys Pro Asp Ser Ala Ala
    435                 440                 445

Asp Leu Thr Trp Ser Tyr Ser Ala Phe Leu Ser Ala Ile Asp Arg Arg
450                 455                 460

Ala Gly Leu Val Pro Pro Ser Trp Arg Ala Ser Val Ala Lys Ser Gln
465                 470                 475                 480

Leu Pro Ser Thr Cys Ser Arg Ile Glu Val Ala Gly Thr Tyr Val Ala
```

```
                         485                 490                 495
Ala Thr Ser Thr Ser Phe Pro Ser Lys Gln Thr Pro Asn Pro Ser Ala
                500                 505                 510

Ala Pro Ser Pro Ser Pro Tyr Pro Thr Ala Cys Ala Asp Ala Ser Glu
            515                 520                 525

Val Tyr Val Thr Phe Asn Glu Arg Val Ser Thr Ala Trp Gly Glu Thr
        530                 535                 540

Ile Lys Val Val Gly Asn Val Pro Ala Leu Gly Asn Trp Asp Thr Ser
545                 550                 555                 560

Lys Ala Val Thr Leu Ser Ala Ser Gly Tyr Lys Ser Asn Asp Pro Leu
                565                 570                 575

Trp Ser Ile Thr Val Pro Ile Lys Ala Thr Gly Ser Ala Val Gln Tyr
            580                 585                 590

Lys Tyr Ile Lys Val Gly Thr Asn Gly Lys Ile Thr Trp Glu Ser Asp
                595                 600                 605

Pro Asn Arg Ser Ile Thr Leu Gln Thr Ala Ser Ser Ala Gly Lys Cys
            610                 615                 620

Ala Ala Gln Thr Val Asn Asp Ser Trp Arg
625                 630

<210> SEQ ID NO 3
<211> LENGTH: 604
<212> TYPE: PRT
<213> ORGANISM: Humicola grisea var. thermoidea

<400> SEQUENCE: 3

Ala Ala Val Asp Thr Phe Ile Asn Thr Glu Lys Pro Ile Ala Trp Asn
1               5                   10                  15

Lys Leu Leu Ala Asn Ile Gly Pro Asn Gly Lys Ala Ala Pro Gly Ala
                20                  25                  30

Ala Gly Val Val Ile Ala Ser Pro Ser Arg Thr Asp Pro Pro Tyr
            35                  40                  45

Phe Phe Thr Trp Thr Arg Asp Ala Ala Leu Val Leu Thr Gly Ile Ile
    50                  55                  60

Glu Ser Leu Gly His Asn Tyr Asn Thr Thr Leu Gln Thr Val Ile Gln
65                  70                  75                  80

Asn Tyr Val Ala Ser Gln Ala Lys Leu Gln Gln Val Ser Asn Pro Ser
                85                  90                  95

Gly Thr Phe Ala Asp Gly Ser Gly Leu Gly Glu Ala Lys Phe Asn Val
            100                 105                 110

Asp Leu Thr Ala Phe Thr Gly Glu Trp Gly Arg Pro Gln Arg Asp Gly
        115                 120                 125

Pro Pro Leu Arg Ala Ile Ala Leu Ile Gln Tyr Ala Lys Trp Leu Ile
    130                 135                 140

Ala Asn Gly Tyr Lys Ser Thr Ala Lys Ser Val Val Trp Pro Val Val
145                 150                 155                 160

Lys Asn Asp Leu Ala Tyr Thr Ala Gln Tyr Trp Asn Glu Thr Gly Phe
                165                 170                 175

Asp Leu Trp Glu Glu Val Pro Gly Ser Ser Phe Phe Thr Ile Ala Ser
            180                 185                 190

Ser His Arg Ala Leu Thr Glu Gly Ala Tyr Leu Ala Ala Gln Leu Asp
        195                 200                 205

Thr Glu Cys Arg Ala Cys Thr Thr Val Ala Pro Gln Val Leu Cys Phe
    210                 215                 220
```

```
Gln Gln Ala Phe Trp Asn Ser Lys Gly Asn Tyr Val Ser Asn Ile
225                 230                 235                 240
Asn Gly Gly Glu Tyr Arg Ser Gly Lys Asp Ala Asn Ser Ile Leu Ala
            245                 250                 255
Ser Ile His Asn Phe Asp Pro Glu Ala Gly Cys Asp Asn Leu Thr Phe
        260                 265                 270
Gln Pro Cys Ser Glu Arg Ala Leu Ala Asn His Lys Ala Tyr Val Asp
    275                 280                 285
Ser Phe Arg Asn Leu Tyr Ala Ile Asn Lys Gly Ile Ala Gln Gly Lys
290                 295                 300
Ala Val Ala Val Gly Arg Tyr Ser Glu Asp Val Tyr Tyr Asn Gly Asn
305                 310                 315                 320
Pro Trp Tyr Leu Ala Asn Phe Ala Ala Glu Gln Leu Tyr Asp Ala
            325                 330                 335
Ile Tyr Val Trp Asn Lys Gln Gly Ser Ile Thr Val Thr Ser Val Ser
        340                 345                 350
Leu Pro Phe Phe Arg Asp Leu Val Ser Val Ser Gly Thr Tyr
    355                 360                 365
Ser Lys Ser Ser Ser Thr Phe Thr Asn Ile Val Asn Ala Val Lys Ala
370                 375                 380
Tyr Ala Asp Gly Phe Ile Glu Val Ala Ala Lys Tyr Thr Pro Ser Asn
385                 390                 395                 400
Gly Ala Leu Ala Glu Gln Tyr Asp Arg Asn Thr Gly Lys Pro Asp Ser
            405                 410                 415
Ala Ala Asp Leu Thr Trp Ser Tyr Ser Ala Phe Leu Ser Ala Ile Asp
        420                 425                 430
Arg Arg Ala Gly Leu Val Pro Pro Ser Trp Arg Ala Ser Val Ala Lys
    435                 440                 445
Ser Gln Leu Pro Ser Thr Cys Ser Arg Ile Glu Val Ala Gly Thr Tyr
450                 455                 460
Val Ala Ala Thr Ser Thr Ser Phe Pro Ser Lys Gln Thr Pro Asn Pro
465                 470                 475                 480
Ser Ala Ala Pro Ser Pro Ser Pro Tyr Pro Thr Ala Cys Ala Asp Ala
            485                 490                 495
Ser Glu Val Tyr Val Thr Phe Asn Glu Arg Val Ser Thr Ala Trp Gly
        500                 505                 510
Glu Thr Ile Lys Val Val Gly Asn Val Pro Ala Leu Gly Asn Trp Asp
    515                 520                 525
Thr Ser Lys Ala Val Thr Leu Ser Ala Ser Gly Tyr Lys Ser Asn Asp
530                 535                 540
Pro Leu Trp Ser Ile Thr Val Pro Ile Lys Ala Thr Gly Ser Ala Val
545                 550                 555                 560
Gln Tyr Lys Tyr Ile Lys Val Gly Thr Asn Gly Lys Ile Thr Trp Glu
            565                 570                 575
Ser Asp Pro Asn Arg Ser Ile Thr Leu Gln Thr Ala Ser Ser Ala Gly
        580                 585                 590
Lys Cys Ala Ala Gln Thr Val Asn Asp Ser Trp Arg
    595                 600
```

<210> SEQ ID NO 4
<211> LENGTH: 2169
<212> TYPE: DNA
<213> ORGANISM: Aspergillus awamori var. kawachi

<400> SEQUENCE: 4

```
atgtcgttcc gatctcttct cgccctgagc ggccttgtct gctcggggtt ggcaagtgtg      60
atttccaagc gcgcgacctt ggattcgtgg ttgagcaacg aagcgaccgt ggcccgtact     120
gcgatcctga ataacatcgg ggcggacggt gcttgggtgt cgggcgcgga ctctggcatt     180
gtcgttgcca gtcccagcac cgataacccg gactgtatgt tttgagttcg gattatgaat     240
gtgtcttggt tgattgatgc tgactggcgt gtcttttgat gattgtagac ttctacacct     300
ggactcgcga ctctggtctc gtcatcaaga ccctcgtcga cctcttccgc aatggagata     360
ctgatctcct ttccaccatt gagcactaca tctcctctca ggcaattatt cagggtgtca     420
gtaacccctc tggtgatctg tccagcggtg gtcttggtga gcccaagttc aatgtcgatg     480
agactgccta caccggttct tggggacggc cgcagcgtga tggtcctgcc ctgagagcaa     540
ctgctatgat cggctttggg cagtggctgc ttgtatgttc tccacctcct tgcgtctgat     600
ctgcaacata tgtagccgac tggtcaggac aatggctaca ccagcgctgc aacagagatt     660
gtttggcccc tcgttaggaa cgacctgtcg tatgtggctc agtactggaa ccagacggga     720
tatggtgtgt ttgattgatc ggggttcaag ggtgtttgtg catcggagct aacttcgcgg     780
tcgcagatct ctgggaagaa gttaatggct cgtccttctt cactattgcc gtgcaacacc     840
gcgccctcgt cgaaggtagt gccttcgcga cggccgtcgg ctcgtcctgc tcctggtgtg     900
attcgcaggc acctcagatt ctctgttact tgcagtcctt ctggaccggc agctacatcc     960
tggccaactt tgacagcagc cgttccggca aggacacaaa caccctcctg ggaagcatcc    1020
acacctttga tcctgaggct ggatgcgacg actccacctt ccagccctgc tccccgcgtg    1080
cgctcgccaa ccataaggag gttgtagact cttccgctc gatctatact ctcaacgatg    1140
gtctcagtga cagtgaggcg gttgcggtcg gtcggtaccc tgaggatagc tactacaacg    1200
gcaacccgtg gttcctgtgc accttggctg ccgcggaaca gctgtacgat gctctgtacc    1260
agtgggacaa gcaggggtcg ttggagatca cagacgtgtc acttgacttc ttcaaggctc    1320
tgtacagtgg tgctgccacc ggcacgtact cttcgtccag ctcgacctat agcagcattg    1380
tgagtgccgt caagactttc gctgatggtt ttgtttctat tgtggtaagt ctacgctaga    1440
cgagcgctca tatttacaga gggtgcgtac taacaggatt aggaaactca cgccgcaagc    1500
aacggctctc tgtctgagca attcgacaag tctgatggcg acgagctttc tgctcgcgat    1560
ctgacctggt cttacgctgc tctgctgacc gccaacaacc gtcgtaattc tgtcgtgccc    1620
ccgtcttggg gtgagacctc tgccagcagc gtgcccggca cctgtgcggc tacctctgcc    1680
tctggtacct acagcagtgt gaccgtcacc tcgtggccga gcatcgtggc tactggtggc    1740
accactacga cggctactac cactggatcg ggcggcgtga cctcgaccag caagaccacc    1800
acaactgcta gtaagaccag caccactacg tcctcgacct cctgcaccac ccccactgcc    1860
gtagctgtga cctttgatct gacggcgacc accacctacg gcgagaacat ctacctggtc    1920
gggtcgatct ctcagctcgg tgactggag accagcgatg catagctct gagcgctgac    1980
aagtacactt ccagcaaccc gctttggtat gtaactgtga ctctgccggc tggtgagtca    2040
tttgagtaca agttcatccg cgtcgagagc gatgactccg tggagtggga gagcgacccg    2100
aaccgggaat acaccgttcc tcaggcgtgc ggcgagtcga ccgcgacggt gaccgacacc    2160
tggcggtag                                                            2169
```

<210> SEQ ID NO 5
<211> LENGTH: 639
<212> TYPE: PRT

<213> ORGANISM: Aspergillus awamori var. kawachi

<400> SEQUENCE: 5

```
Met Ser Phe Arg Ser Leu Leu Ala Leu Ser Gly Leu Val Cys Ser Gly
1               5                   10                  15

Leu Ala Ser Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Ile Lys Thr Leu Val Asp Leu Phe Arg Asn Gly Asp Thr
                85                  90                  95

Asp Leu Leu Ser Thr Ile Glu His Tyr Ile Ser Ser Gln Ala Ile Ile
            100                 105                 110

Gln Gly Val Ser Asn Pro Ser Gly Asp Leu Ser Ser Gly Gly Leu Gly
        115                 120                 125

Glu Pro Lys Phe Asn Val Asp Glu Thr Ala Tyr Thr Gly Ser Trp Gly
130                 135                 140

Arg Pro Gln Arg Asp Gly Pro Ala Leu Arg Ala Thr Ala Met Ile Gly
145                 150                 155                 160

Phe Gly Gln Trp Leu Leu Asp Asn Gly Tyr Thr Ser Ala Ala Thr Glu
                165                 170                 175

Ile Val Trp Pro Leu Val Arg Asn Asp Leu Ser Tyr Val Ala Gln Tyr
            180                 185                 190

Trp Asn Gln Thr Gly Tyr Asp Leu Trp Glu Glu Val Asn Gly Ser Ser
        195                 200                 205

Phe Phe Thr Ile Ala Val Gln His Arg Ala Leu Val Glu Gly Ser Ala
210                 215                 220

Phe Ala Thr Ala Val Gly Ser Ser Cys Ser Trp Cys Asp Ser Gln Ala
225                 230                 235                 240

Pro Gln Ile Leu Cys Tyr Leu Gln Ser Phe Trp Thr Gly Ser Tyr Ile
                245                 250                 255

Leu Ala Asn Phe Asp Ser Ser Arg Ser Gly Lys Asp Thr Asn Thr Leu
            260                 265                 270

Leu Gly Ser Ile His Thr Phe Asp Pro Glu Ala Gly Cys Asp Asp Ser
        275                 280                 285

Thr Phe Gln Pro Cys Ser Pro Arg Ala Leu Ala Asn His Lys Glu Val
290                 295                 300

Val Asp Ser Phe Arg Ser Ile Tyr Thr Leu Asn Asp Gly Leu Ser Asp
305                 310                 315                 320

Ser Glu Ala Val Ala Val Gly Arg Tyr Pro Glu Asp Ser Tyr Tyr Asn
                325                 330                 335

Gly Asn Pro Trp Phe Leu Cys Thr Leu Ala Ala Ala Glu Gln Leu Tyr
            340                 345                 350

Asp Ala Leu Tyr Gln Trp Asp Lys Gln Gly Ser Leu Glu Ile Thr Asp
        355                 360                 365

Val Ser Leu Asp Phe Phe Lys Ala Leu Tyr Ser Gly Ala Ala Thr Gly
370                 375                 380

Thr Tyr Ser Ser Ser Ser Ser Thr Tyr Ser Ser Ile Val Ser Ala Val
385                 390                 395                 400
```

```
Lys Thr Phe Ala Asp Gly Phe Val Ser Ile Val Glu Thr His Ala Ala
                405                 410                 415

Ser Asn Gly Ser Leu Ser Glu Gln Phe Asp Lys Ser Asp Gly Asp Glu
            420                 425                 430

Leu Ser Ala Arg Asp Leu Thr Trp Ser Tyr Ala Ala Leu Leu Thr Ala
        435                 440                 445

Asn Asn Arg Arg Asn Ser Val Val Pro Pro Ser Trp Gly Glu Thr Ser
450                 455                 460

Ala Ser Ser Val Pro Gly Thr Cys Ala Ala Thr Ser Ala Ser Gly Thr
465                 470                 475                 480

Tyr Ser Ser Val Thr Val Thr Ser Trp Pro Ser Ile Val Ala Thr Gly
                485                 490                 495

Gly Thr Thr Thr Thr Ala Thr Thr Gly Ser Gly Gly Val Thr Ser
                500                 505                 510

Thr Ser Lys Thr Thr Thr Thr Ala Ser Lys Thr Ser Thr Thr Thr Ser
        515                 520                 525

Ser Thr Ser Cys Thr Thr Pro Thr Ala Val Ala Val Thr Phe Asp Leu
        530                 535                 540

Thr Ala Thr Thr Thr Tyr Gly Glu Asn Ile Tyr Leu Val Gly Ser Ile
545                 550                 555                 560

Ser Gln Leu Gly Asp Trp Glu Thr Ser Asp Gly Ile Ala Leu Ser Ala
                565                 570                 575

Asp Lys Tyr Thr Ser Ser Asn Pro Leu Trp Tyr Val Thr Val Thr Leu
                580                 585                 590

Pro Ala Gly Glu Ser Phe Glu Tyr Lys Phe Ile Arg Val Glu Ser Asp
            595                 600                 605

Asp Ser Val Glu Trp Glu Ser Asp Pro Asn Arg Glu Tyr Thr Val Pro
610                 615                 620

Gln Ala Cys Gly Glu Ser Thr Ala Thr Val Thr Asp Thr Trp Arg
625                 630                 635

<210> SEQ ID NO 6
<211> LENGTH: 615
<212> TYPE: PRT
<213> ORGANISM: Aspergillus awamori var. kawachi

<400> SEQUENCE: 6

Ala Thr Leu Asp Ser Trp Leu Ser Asn Glu Ala Thr Val Ala Arg Thr
1               5                   10                  15

Ala Ile Leu Asn Asn Ile Gly Ala Asp Gly Ala Trp Val Ser Gly Ala
            20                  25                  30

Asp Ser Gly Ile Val Val Ala Ser Pro Ser Thr Asp Asn Pro Asp Tyr
        35                  40                  45

Phe Tyr Thr Trp Thr Arg Asp Ser Gly Leu Val Ile Lys Thr Leu Val
    50                  55                  60

Asp Leu Phe Arg Asn Gly Asp Thr Asp Leu Leu Ser Thr Ile Glu His
65                  70                  75                  80

Tyr Ile Ser Ser Gln Ala Ile Ile Gln Gly Val Ser Asn Pro Ser Gly
                85                  90                  95

Asp Leu Ser Gly Gly Leu Gly Glu Pro Lys Phe Asn Val Asp Glu
            100                 105                 110

Thr Ala Tyr Thr Gly Ser Trp Gly Arg Pro Gln Arg Asp Gly Pro Ala
        115                 120                 125

Leu Arg Ala Thr Ala Met Ile Gly Phe Gly Gln Trp Leu Leu Asp Asn
130                 135                 140
```

-continued

```
Gly Tyr Thr Ser Ala Ala Thr Glu Ile Val Trp Pro Leu Val Arg Asn
145                 150                 155                 160

Asp Leu Ser Tyr Val Ala Gln Tyr Trp Asn Gln Thr Gly Tyr Asp Leu
                165                 170                 175

Trp Glu Val Asn Gly Ser Ser Phe Phe Thr Ile Ala Val Gln His
            180                 185                 190

Arg Ala Leu Val Glu Gly Ser Ala Phe Ala Thr Ala Val Gly Ser Ser
            195                 200                 205

Cys Ser Trp Cys Asp Ser Gln Ala Pro Gln Ile Leu Cys Tyr Leu Gln
210                 215                 220

Ser Phe Trp Thr Gly Ser Tyr Ile Leu Ala Asn Phe Asp Ser Ser Arg
225                 230                 235                 240

Ser Gly Lys Asp Thr Asn Thr Leu Leu Gly Ser Ile His Thr Phe Asp
                245                 250                 255

Pro Glu Ala Gly Cys Asp Asp Ser Thr Phe Gln Pro Cys Ser Pro Arg
            260                 265                 270

Ala Leu Ala Asn His Lys Glu Val Val Asp Ser Phe Arg Ser Ile Tyr
            275                 280                 285

Thr Leu Asn Asp Gly Leu Ser Asp Ser Glu Ala Val Ala Val Gly Arg
290                 295                 300

Tyr Pro Glu Asp Ser Tyr Tyr Asn Gly Asn Pro Trp Phe Leu Cys Thr
305                 310                 315                 320

Leu Ala Ala Ala Glu Gln Leu Tyr Asp Ala Leu Tyr Gln Trp Asp Lys
                325                 330                 335

Gln Gly Ser Leu Glu Ile Thr Asp Val Ser Leu Asp Phe Phe Lys Ala
            340                 345                 350

Leu Tyr Ser Gly Ala Ala Thr Gly Thr Tyr Ser Ser Ser Ser Thr
            355                 360                 365

Tyr Ser Ser Ile Val Ser Ala Val Lys Thr Phe Ala Asp Gly Phe Val
370                 375                 380

Ser Ile Val Glu Thr His Ala Ala Ser Asn Gly Ser Leu Ser Glu Gln
385                 390                 395                 400

Phe Asp Lys Ser Asp Gly Asp Glu Leu Ser Ala Arg Asp Leu Thr Trp
                405                 410                 415

Ser Tyr Ala Ala Leu Leu Thr Ala Asn Asn Arg Arg Asn Ser Val Val
            420                 425                 430

Pro Pro Ser Trp Gly Glu Thr Ser Ala Ser Val Pro Gly Thr Cys
            435                 440                 445

Ala Ala Thr Ser Ala Ser Gly Thr Tyr Ser Ser Val Thr Val Thr Ser
450                 455                 460

Trp Pro Ser Ile Val Ala Thr Gly Gly Thr Thr Thr Ala Thr Thr
465                 470                 475                 480

Thr Gly Ser Gly Gly Val Thr Ser Thr Ser Lys Thr Thr Thr Thr Ala
                485                 490                 495

Ser Lys Thr Ser Thr Thr Thr Ser Ser Thr Cys Thr Thr Pro Thr
            500                 505                 510

Ala Val Ala Val Thr Phe Asp Leu Thr Ala Thr Thr Tyr Gly Glu
            515                 520                 525

Asn Ile Tyr Leu Val Gly Ser Ile Ser Gln Leu Gly Asp Trp Glu Thr
530                 535                 540

Ser Asp Gly Ile Ala Leu Ser Ala Asp Lys Tyr Thr Ser Ser Asn Pro
545                 550                 555                 560
```

-continued

```
Leu Trp Tyr Val Thr Val Thr Leu Pro Ala Gly Glu Ser Phe Glu Tyr
            565                 570                 575

Lys Phe Ile Arg Val Glu Ser Asp Asp Ser Val Glu Trp Glu Ser Asp
        580                 585                 590

Pro Asn Arg Glu Tyr Thr Val Pro Gln Ala Cys Gly Glu Ser Thr Ala
            595                 600                 605

Thr Val Thr Asp Thr Trp Arg
        610                 615

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
caacatgcat accttctcca agctcctc                                          28

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
ttaacgccac gaatcattca ccgtc                                             25

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
caccatgtcg ttccgatctc ttctc                                             25

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
ctaccgccag gtgtcggtca c                                                 21

<210> SEQ ID NO 11
<211> LENGTH: 10739
<212> TYPE: DNA
<213> ORGANISM: Artificial Sequence
<220> FEATURE:
<223> OTHER INFORMATION: pTrex3g_N13 plasmid sequence

<400> SEQUENCE: 11
aagcttacta gtacttctcg agctctgtac atgtccggtc gcgacgtacg cgtatcgatg        60
gcgccagctg caggcggccg cctgcagcca cttgcagtcc cgtggaattc tcacggtgaa       120
tgtaggcctt ttgtagggta ggaattgtcc ctcaagcacc cccaacctcc attacgcctc       180
ccccatagag ttcccaatca gtgagtcatg gcactgttct caaatagatt ggggagaagt       240
tgacttccgc ccagagctga aggtcgcaca accgcatgat atagggtcgg caacggcaaa       300
```

```
aaagcacgtg gctcaccgaa aagcaagatg tttgcgatct aacatccagg aacctggata      360
catccatcat cacgcacgac cactttgatc tgctggtaaa ctcgtattcg ccctaaaccg      420
aagtgcgtgg taaatctaca cgtgggcccc tttcggtata ctgcgtgtgt cttctctagg      480
tgccattctt ttcccttcct ctagtgttga attgtttgtg ttggagtccg agctgtaact      540
acctctgaat ctctggagaa tggtggacta acgactaccg tgcacctgca tcatgtatat      600
aatagtgatc ctgagaaggg gggttttggag caatgtggga ctttgatggt catcaaacaa      660
agaacgaaga cgcctctttt gcaaagtttt gtttcggcta cggtgaagaa ctggatactt      720
gttgtgtctt ctgtgtattt ttgtggcaac aagaggccag agacaatcta ttcaaacacc      780
aagcttgctc ttttgagcta caagaacctg tggggtatat atctagagtt gtgaagtcgg      840
taatcccgct gtatagtaat acgagtcgca tctaaatact ccgaagctgc tgcgaacccg      900
gagaatcgag atgtgctgga aagcttctag cgagcggcta aattagcatg aaaggctatg      960
agaaattctg gagacggctt gttgaatcat ggcgttccat tcttcgacaa gcaaagcgtt     1020
ccgtcgcagt agcaggcact cattcccgaa aaaactcgga gattcctaag tagcgatgga     1080
accggaataa tataataggc aatacattga gttgcctcga cggttgcaat gcaggggtac     1140
tgagcttgga cataactgtt ccgtacccca cctcttctca acctttggcg tttccctgat     1200
tcagcgtacc cgtacaagtc gtaatcacta ttaacccaga ctgaccggac gtgttttgcc     1260
cttcatttgg agaaataatg tcattgcgat gtgtaatttg cctgcttgac cgactggggc     1320
tgttcgaagc ccgaatgtag gattgttatc cgaactctgc tcgtagaggc atgttgtgaa     1380
tctgtgtcgg gcaggacacg cctcgaaggt tcacggcaag ggaaaccacc gatagcagtg     1440
tctagtagca acctgtaaag ccgcaatgca gcatcactgg aaaatacaaa ccaatggcta     1500
aaagtacata agttaatgcc taaagaagtc atataccagc ggctaataat tgtacaatca     1560
agtggctaaa cgtaccgtaa tttgccaacg gcttgtgggg ttgcagaagc aacggcaaag     1620
ccccacttcc ccacgtttgt ttcttcactc agtccaatct cagctggtga tcccccaatt     1680
gggtcgcttg tttgttccgg tgaagtgaaa gaagacagag gtaagaatgt ctgactcgga     1740
gcgttttgca tacaaccaag ggcagtgatg gaagacagtg aaatgttgac attcaaggag     1800
tatttagcca gggatgcttg agtgtatcgt gtaaggaggt ttgtctgccg atacgacgaa     1860
tactgtatag tcacttctga tgaagtggtc catattgaaa tgtaaagtcg gcactgaaca     1920
ggcaaaagat tgagttgaaa ctgcctaaga tctcgggccc tcgggccttc ggcctttggg     1980
tgtacatgtt tgtgctccgg gcaaatgcaa agtgtggtag gatcgaacac actgctgcct     2040
ttaccaagca gctgagggta tgtgataggc aaatgttcag gggccactgc atggtttcga     2100
atagaaagag aagcttagcc aagaacaata gccgataaag atagcctcat taaacggaat     2160
gagctagtag gcaaagtcag cgaatgtgta tatataaagg ttcgaggtcc gtgcctccct     2220
catgctctcc ccatcactc atcaactcag atcctccagg agacttgtac accatctttt     2280
gaggcacaga aacccaatag tcaaccatca caagtttgta caaaaaagca ggctccgcgg     2340
ccgccccctt caacatgcat accttctcca agctcctcgt cctgggctct gccgtccagt     2400
ctgccctcgg gcggcctcac ggctcttcgc gtctccagga acgcgctgcc gttgatacct     2460
tcatcaacac cgagaagccc atcgcatgga acaagctgct cgccaacatc ggccctaacg     2520
gcaaagccgc tcccggtgcc gccgccgcg ttgtgattgc cagcccttcc aggacggacc     2580
ctccttgtac gtggtggcat ggaatggacc caagagactg gttttagatg aaagagagtt     2640
```

```
tctgctaacc gccacaccca gacttcttca cctggacccg cgatgccgcc ctggtcctca    2700
ccggcatcat cgagtcccct tggccacaact acaacaccac cctgcagacc gtcatccaga    2760
actacgtcgc gtcgcaggcc aagctgcagc aggtctcgaa cccctcggga accttcgccg    2820
acggctcggg tctcggtgag gccaagttca atgtcgacct cactgccttc actggcgaat    2880
ggggtcgccc tcagagggac ggcccgcccc tgcgcgccat cgctctcatc cagtacgcca    2940
agtggctgat cgccaacggc tacaagagca cggccaagag cgtcgtctgg cccgtcgtca    3000
agaacgatct cgcctacacg gcccagtact ggaacgagac cggcttcgat ctctgggagg    3060
aggtccccgg cagctcgttc tttaccatcg ccagctctca caggggtgag tcatttattg    3120
ttcagtgttt tctcattgaa taattaccgg aatgccactg acgccaaaca gctctgactg    3180
agggtgctta cctcgccgct cagctcgaca ccgagtgccg cgcctgcacg accgtcgccc    3240
ctcaggttct gtgcttccag caggccttct ggaactccaa gggcaactat gtcgtctcca    3300
acagtaagat ccctcaccca acaaaaaaaa tcgaaaagga acgttagctg acccttctag    3360
tcaacggcgg cgagtatcgc tccggcaagg acgccaactc gatcctggcg tccatccaca    3420
acttcgaccc tgaggccggc tgcgacaacc tgaccttcca gccctgcagc gagcgcgccc    3480
tggccaacca caaggcctat gtcgactcgt ccgcaacctc ctacgccatc aacaagggca    3540
tcgcccaggg caaggccgtt gccgtcggcc gctactcgga ggatgtctac tacaacggca    3600
acccgtggta cctggccaac tttgccgccg ccgagcagct ctacgacgcc atctacgtgt    3660
ggaacaagca gggctccatc accgtgacct cggtctccct gcccttcttc cgcgaccttg    3720
tctcgtcggt cagcaccggc acctactcca agagcagctc gaccttcacc aacatcgtca    3780
acgccgtcaa ggcctacgcc gacggcttca tcgaggtggc ggccaagtac accccgtcca    3840
acggcgcgct cgccgagcag tacgaccgca acacgggcaa gcccgactcg gccgccgacc    3900
tgacgtggtc gtactcggcc ttcctctcgg ccatcgaccg ccgcgcgggt ctcgtccccc    3960
cgagctggcg ggccagcgtg gccaagagcc agctgccgtc cacctgctcg cgcatcgagg    4020
tcgccggcac ctacgtcgcc gccacgagca cctcgttccc gtccaagcag accccgaacc    4080
cctccgcggc gccctcccccg tcccccttacc cgaccgcctg cgcggacgct agcgaggtgt    4140
acgtcacctt caacgagcgc gtgtcgaccg cgtggggcga gaccatcaag gtggtgggca    4200
acgtgccggc gctggggaac tgggacacgt ccaaggcggt gaccctgtcg gccagcgggt    4260
acaagtcgaa tgatcccctc tggagcatca cggtgcccat caaggcgacg ggctcggccg    4320
tgcagtacaa gtatatcaag gtcggcacca acgggaagat tacttgggag tcggacccca    4380
acaggagcat taccctgcag acggcgtcgt ctgcgggcaa gtgcgccgcg cagacggtga    4440
atgattcgtg gcgttaaaag ggtgggcgcg ccgacccagc tttcttgtac aaagtggtga    4500
tcgcgccagc tccgtgcgaa agcctgacgc accggtagat tcttggtgag cccgtatcat    4560
gacggcggcg ggagctacat ggccccgggt gatttatttt ttttgtatct acttctgacc    4620
cttttcaaat atacggtcaa ctcatctttc actggagatg cggcctgctt ggtattgcga    4680
tgttgtcagc ttggcaaatt gtggctttcg aaaacacaaa acgattcctt agtagccatg    4740
cattttaaga taacggaata gaagaaagag gaaattaaaa aaaaaaaaaaa aacaaacatc    4800
ccgttcataa cccgtagaat cgccgctctt cgtgtatccc agtaccagtt tattttgaat    4860
agctcgcccg ctggagagca tcctgaatgc aagtaacaac cgtagaggct gacacggcag    4920
gtgttgctag ggagcgtcgt gttctacaag gccagcgtc ttcgcggttg atatatatgt    4980
atgtttgact gcaggctgct cagcgacgac agtcaagttc gccctcgctg cttgtgcaat    5040
```

```
aatcgcagtg gggaagccac accgtgactc ccatctttca gtaaagctct gttggtgttt    5100
atcagcaata cacgtaattt aaactcgtta gcatggggct gatagcttaa ttaccgttta    5160
ccagtgccat ggttctgcag cttttccttg cccgtaaaat tcggcgaagc cagccaatca    5220
ccagctaggc accagctaaa ccctataatt agtctcttat caacaccatc cgctcccccg    5280
ggatcaatga ggagaatgag ggggatgcgg ggctaaagaa gcctacataa ccctcatgcc    5340
aactcccagt ttacactcgt cgagccaaca tcctgactat aagctaacac agaatgcctc    5400
aatcctggga agaactggcc gctgataagc gcgcccgcct cgcaaaaacc atccctgatg    5460 aatgaaagt ccagacgctg cctgcggaag acagcgttat tgatttccca agaaatcgg     5520 ggatcctttc agaggccgaa ctgaagatca cagaggcctc cgctgcagat cttgtgtcca    5580
agctggcggc cggagagttg acctcggtgg aagttacgct agcattctgt aaacgggcag    5640
caatcgccca gcagttagta gggtcccctc tacctctcag ggagatgtaa caacgccacc    5700
ttatgggact atcaagctga cgctggcttc tgtgcagaca aactgcgccc acgagttctt    5760
ccctgacgcc gctctcgcgc aggcaaggga actcgatgaa tactacgcaa agcacaagag    5820
acccgttggt ccactccatg gcctccccat ctctctcaaa gaccagcttc gagtcaaggt    5880
acaccgttgc ccctaagtcg ttagatgtcc cttttttgtca gctaacatat gccaccaggg   5940
ctacgaaaca tcaatgggct acatctcatg gctaaacaag tacgacgaag gggactcggt    6000
tctgacaacc atgctccgca agccggtgc cgtcttctac gtcaagacct ctgtcccgca    6060
gaccctgatg gtctgcgaga cagtcaacaa catcatcggg cgcaccgtca acccacgcaa    6120
caagaactgg tcgtgcggcg gcagttctgg tggtgagggt gcgatcgttg ggattcgcrv    6180
tggtggcgtc atcggtgtag gaacggatat cggtggctcg attcgagtgc cggccgcgtt    6240
caacttcctg tacggtctaa ggccgagtca tgggcggctg ccgtatgcaa agatggcgaa    6300
cagcatggag ggtcaggaga cggtgcacag cgttgtcggg ccgattacgc actctgttga    6360
gggtgagtcc ttcgcctctt ccttcttttc ctgctctata ccaggcctcc actgtcctcc    6420
tttcttgctt tttatactat atacgagacc ggcagtcact gatgaagtat gttagacctc    6480
cgcctcttca ccaaatccgt cctcggtcag gagccatgga aatacgactc caaggtcatc    6540
cccatgccct ggcgccagtc cgagtcggac attattgcct ccaagatcaa gaacggcggg    6600
ctcaatatcg gctactacaa cttcgacggc aatgtccttc cacaccctcc tatcctgcgc    6660
ggcgtggaaa ccaccgtcgc cgcactcgcc aaagccggtc acaccgtgac cccgtggacg    6720
ccatacaagc acgatttcgg ccacgatctc atctcccata tctacgcggc tgacggcagc    6780
crvgccgacg taatgcgcga tatcagtgca tccggcgagc cggcgattcc aaatatcaaa    6840
gacctactga acccgaacat caaagctgtt aacatgaacg agctctggga cacgcatctc    6900
cagaagtgga attaccagat ggagtacctt gagaaatggc gggaggctga agaaaaggcc    6960
gggaaggaac tggacgccat catcgcgccg attacgccta ccgctgcggt acggcatgac    7020
cagttccggt actatgggta tgcctctgtg atcaacctgc tggatttcac gagcgtggtt    7080
gttccggtta ccttttgcgga taagaacatc gataagaaga atgagagttt caaggcggtt    7140
agtgagcttg atgccctcgt gcaggaagag tatgatccgg aggcgtacca tggggcaccg    7200
gttgcagtgc aggttatcgg acggagactc agtgaagaga ggacgttggc gattgcagag    7260
gaagtgggga agttgctggg aaatgtggtg actccatagc taataagtgt cagatagcaa    7320
tttgcacaag aaatcaatac cagcaactgt aaataagcgc tgaagtgacc atgccatgct    7380
```

```
acgaaagagc agaaaaaaac ctgccgtaga accgaagaga tatgacacgc ttccatctct    7440
caaaggaaga atcccttcag ggttgcgttt ccagtctaga cacgtataac ggcacaagtg    7500
tctctcacca aatgggttat atctcaaatg tgatctaagg atggaaagcc cagaatatcg    7560
atcgcgcgca gatccatata tagggcccgg gttataatta cctcaggtcg acgtcccatg    7620
gccattcgaa ttcgtaatca tggtcatagc tgtttcctgt gtgaaattgt tatccgctca    7680
caattccaca acatacga gccggaagca taaagtgtaa agcctggggt gcctaatgag    7740
tgagctaact cacattaatt gcgttgcgct cactgcccgc tttccagtcg ggaaacctgt    7800
cgtgccagct gcattaatga atcggccaac gcgcgggag aggcggtttg cgtattgggc    7860
gctcttccgc ttcctcgctc actgactcgc tgcgctcggt cgttcggctg cggcgagcgg    7920
tatcagctca ctcaaaggcg gtaatacggt tatccacaga atcaggggat aacgcaggaa    7980
agaacatgtg agcaaaaggc cagcaaaagg ccaggaaccg taaaaaggcc gcgttgctgg    8040
cgttttccca taggctccgc cccctgacg agcatcacaa aaatcgacgc tcaagtcaga    8100
ggtggcgaaa cccgacagga ctataaagat accaggcgtt tccccctgga agctccctcg    8160
tgcgctctcc tgttccgacc ctgccgctta ccggatacct gtccgccttt ctcccttcgg    8220
gaagcgtggc gctttctcat agctcacgct gtaggtatct cagttcggtg taggtcgttc    8280
gctccaagct gggctgtgtg cacgaacccc ccgttcagcc cgaccgctgc gccttatccg    8340
gtaactatcg tcttgagtcc aacccggtaa gacacgactt atcgccactg gcagcagcca    8400
ctggtaacag gattagcaga gcgaggtatg taggcggtgc tacagagttc ttgaagtggt    8460
ggcctaacta cggctacact agaagaacag tatttggtat ctgcgctctg ctgaagccag    8520
ttaccttcgg aaaaagagtt ggtagctctt gatccggcaa acaaaccacc gctggtagcg    8580
gtggtttttt tgtttgcaag cagcagatta cgcgcagaaa aaaaggatct caagaagatc    8640
ctttgatctt ttctacgggg tctgacgctc agtggaacga aaactcacgt taagggattt    8700
tggtcatgag attatcaaaa aggatcttca cctagatcct tttaaattaa aaatgaagtt    8760
ttaaatcaat ctaaagtata tatgagtaaa cttggtctga cagttaccaa tgcttaatca    8820
gtgaggcacc tatctcagcg atctgtctat ttcgttcatc catagttgcc tgactccccg    8880
tcgtgtagat aactacgata cgggagggct taccatctgg ccccagtgct gcaatgatac    8940
cgcgagaccc acgctcaccg gctccagatt tatcagcaat aaaccagcca gccggaaggg    9000
ccgagcgcag aagtggtcct gcaactttat ccgcctccat ccagtctatt aattgttgcc    9060
gggaagctag agtaagtagt tcgccagtta atagtttgcg caacgttgtt gccattgcta    9120
caggcatcgt ggtgtcacgc tcgtcgtttg gtatggcttc attcagctcc ggttcccaac    9180
gatcaaggcg agttacatga tcccccatgt tgtgcaaaaa agcggttagc tccttcggtc    9240
ctccgatcgt tgtcagaagt aagttggccg cagtgttatc actcatggtt atggcagcac    9300
tgcataattc tcttactgtc atgccatccg taagatgctt ttctgtgact ggtgagtact    9360
caaccaagtc attctgagaa tagtgtatgc ggcgaccgag ttgctcttgc ccggcgtcaa    9420
tacgggataa taccgcgcca catagcagaa ctttaaaagt gctcatcatt ggaaaacgtt    9480
cttcggggcg aaaactctca aggatcttac cgctgttgag atccagttcg atgtaaccca    9540
ctcgtgcacc caactgatct tcagcatctt ttactttcac cagcgtttct gggtgagcaa    9600
aaacaggaag gcaaaatgcc gcaaaaaagg gaataagggc gacacggaaa tgttgaatac    9660
tcatactctt cctttttcaa tattattgaa gcatttatca gggttattgt ctcatgagcg    9720
gatacatatt tgaatgtatt tagaaaaata aacaaatagg ggttccgcgc acatttcccc    9780
```

```
gaaaagtgcc acctgacgtc taagaaacca ttattatcat gacattaacc tataaaata   9840 ggcgtatcac gaggcccttt cgtctcgcgc gtttcggtga tgacggtgaa aacctctgac  9900
acatgcagct cccggagacg gtcacagctt gtctgtaagc ggatgccggg agcagacaag  9960
cccgtcaggg cgcgtcagcg ggtgttggcg ggtgtcgggg ctggcttaac tatgcggcat  10020
cagagcagat tgtactgaga gtgcaccata aaattgtaaa cgttaatatt ttgttaaaat  10080
tcgcgttaaa tttttgttaa atcagctcat tttttaacca ataggccgaa atcggcaaaa  10140
tcccttataa atcaaaagaa tagcccgaga tagggttgag tgttgttcca gtttggaaca  10200
agagtccact attaaagaac gtggactcca acgtcaaagg gcgaaaaacc gtctatcagg  10260
gcgatggccc actacgtgaa ccatcaccca aatcaagttt tttggggtcg aggtgccgta  10320
aagcactaaa tcggaaccct aaagggagcc cccgatttag agcttgacgg ggaaagccgg  10380
cgaacgtggc gagaaaggaa gggaagaaag cgaaaggagc gggcgctagg gcgctggcaa  10440
gtgtagcggt cacgctgcgc gtaaccacca cacccgccgc gcttaatgcg ccgctacagg  10500
gcgcgtacta tggttgcttt gacgtatgcg gtgtgaaata ccgcacagat gcgtaaggag  10560
aaaataccgc atcaggcgcc attcgccatt caggctgcgc aactgttggg aagggcgatc  10620
ggtgcgggcc tcttcgctat tacgccagct ggcgaaaggg ggatgtgctg caaggcgatt  10680
aagttgggta acgccagggt tttcccagtc acgacgttgt aaaacgacgg ccagtgccc   10739
```

EXPRESSION OF GRANULAR STARCH HYDROLYZING ENZYME IN TRICHODERMA

CROSS-REFERENCE TO RELATED APPLICATIONS

The present application is a divisional of U.S. patent application Ser. No. 11/960,259, filed Dec. 19, 2007, which is a divisional of U.S. patent application Ser. No. 11/633,309, filed Dec. 4, 2006, now U.S. Pat. No. 7,335,503, which is a Continuation of U.S. patent application Ser. No. 10/992,187, filed Nov. 18, 2004, now U.S. Pat. No. 7,262,041, which claims priority to U.S. Provisional Patent Appln. Ser. No. 60/524,279, filed Nov. 21, 2003; U.S. Provisional Patent Appln. No. 60/531,953, filed Dec. 22, 2003; and U.S. Provisional Patent Appln. No. 60/566,358, filed Apr. 28, 2004.

SEQUENCE LISTING

The sequence listing submitted via EFS, in compliance with 37 C.F.R. §1.52(e), is incorporated herein by reference. The sequence listing text file submitted via EFS contains the file "30820US-C1-D1-D1_SEQLIST.txt" created on Nov. 18, 2013, which is 41,146 bytes in size.

FIELD OF THE INVENTION

The present invention relates to filamentous fungal host cells useful for the production of granular starch hydrolyzing enzymes having glucoamylase activity (GSHE), wherein the GSHE is derived from a strain of *Humicola grisea* or a strain of *Aspergillus awamori*. More specifically, the invention relates to the expression of a heterologous polynucleotide encoding a GSHE in a *Trichoderma* host and particularly in a *Trichoderma reesei* host.

BACKGROUND OF THE INVENTION

Industrial fermentations predominately use glucose as a feed stock for the production of a multitude of proteins, enzymes, alcohols and other chemicals. In many applications, the glucose is produced by the enzymatic conversion of starch. This conversion is frequently accomplished by a two-step process. The first step is a liquefaction step, wherein an insoluble granular starch substrate is slurried in water, gelatinized with heat and hydrolyzed by a thermostable alpha amylase (e.g., E.C. 3.2.1.1: 1,4-alpha-D-glucan glucanohydrolase) in the presence of calcium. The second step is a saccharification step, wherein the soluble dextrins (sugars) produced in the first step are further hydrolyzed to glucose by an enzyme having glucoamylase (e.g., E.C. 3.2.1.3: 1,4-alpha-D-glucan glucohydrolase) activity. Glucoamylases catalyze the release of glucose from the non-reducing ends of starch. Glucose may then be used as an end product or used as a precursor to be converted to other commercially important end products, such as fructose, ethanol, ascorbic acid (ASA) intermediates and/or 1,3-propanediol.

Therefore, glucoamylases, which are involved in the conversion of starch to sugar are extremely important industrial enzymes. Glucoamylases may be obtained from bacteria, plants and fungi. However, preferred glucoamylases are derived from fungal strains. Examples of fungal glucoamylases include those obtained from strains of *Aspergillus, Rhizopus, Humicola* and *Mucor* (See, WO 92/00381 and WO 00/04136).

Various glucoamylases have been commercialized, including *Aspergillus niger* glucoamylase (e.g., trade name OPTIDEX L-400® from Genencor International Inc. and trade name AMG from Novo Nordisk) and *Rhizopus* (e.g., trade name CU.CONC from Shin Nihon Chemicals, Japan and trade name GLUCZYME from Amano Pharmaceuticals, Japan).

Certain thermophilic and mesophilic fungi, and particularly strains of *Humicola grisea* and *Aspergillus awamori*, produce an enzyme having both glucoamylase activity and the ability to hydrolyze raw starch. These glucoamylases are referred to as granular starch hydrolyzing enzymes (GSHE) and are also known in the art as raw starch hydrolyzing (RSH) enzymes. Additionally, while these enzymes will hydrolyze thinned starch hydrolyzate to glucose in a manner similar to other known glucoamylases, they frequently have a pH optimum in the range of 5.0 to 7.0 as compared to a pH optimum of less than 5.0 for widely used glucoamylase preparations (See, Tosi et al., (1993) *Can. J. Microbiol.*, 39: 846-851).

BRIEF SUMMARY OF THE INVENTION

Since glucoamylases and in particular granular starch hydrolyzing enzymes are important enzymes used industrially for the conversion of starch to glucose, processes providing increased expression and production of these enzymes are highly desirable. In addition, granular starch hydrolyzing enzymes having improved characteristics, such as increased specific activity, different pH ranges, and/or different levels of glycosylation may be particularly advantageous in industrial processes.

It is a primary object of this invention to provide a filamentous fungal strain transformed with a heterologous polynucleotide encoding a granular starch hydrolyzing enzyme, especially a *Trichoderma* strain and more specifically a strain of *T. reesei*, which expresses and secretes granular starch hydrolyzing enzyme into its culture medium.

In one aspect, the invention provides a recombinant *Trichoderma* cell comprising a heterologous polynucleotide encoding a granular starch hydrolyzing enzyme (GSHE). In one embodiment, the recombinant *Trichoderma* cell includes a heterologous polynucleotide encoding a GSHE having at least 80% sequence identity to the sequence set forth in SEQ ID NO: 3 or the sequence set forth in SEQ ID NO: 6. In a second embodiment, the recombinant *Trichoderma* cell includes a heterologous polynucleotide encoding a GSHE having at least 90% sequence identity to the sequence set forth in SEQ ID NO: 3 or the sequence set forth in SEQ ID NO: 6. In a third embodiment, the recombinant *Trichoderma* cell includes a heterologous polynucleotide encoding a GSHE having at least 95% sequence identity to the sequence set forth in SEQ ID NO: 3 or the sequence set forth in SEQ ID NO: 6. In a fourth embodiment, the recombinant *Trichoderma* cell includes a heterologous polynucleotide encoding a GSHE having the sequence set forth in SEQ ID NO: 3 or the sequence set forth in SEQ ID NO: 6. In another embodiment, the recombinant *Trichoderma* cell includes a heterologous polynucleotide encoding a GSHE wherein the polynucleotide has at least 90% sequence identity with the sequence set forth in SEQ ID NO: 1 or the sequence set forth in SEQ ID NO: 4. In another embodiment, the recombinant *Trichoderma* cell includes a heterologous polynucleotide encoding a GSHE wherein the polynucleotide has the sequence set forth in SEQ ID NO: 1 or the sequence set forth in SEQ ID NO: 4. In a preferred embodiment, the recombinant *Trichoderma* cell is a *T. reesei* cell. In certain embodiments of this aspect the heterologous polynucleotide encodes a GSHE that is expressed at a level of greater than 1 g/L.

In a second aspect, the invention provides methods for producing a recombinantly expressed granular starch hydrolyzing enzyme (GSHE) in a filamentous fungal cell which comprises cultivating in a suitable culture medium a filamentous fungal host cell transformed with a DNA construct comprising a promoter having transcriptional activity in the filamentous fungal host cell operably linked to a heterologous polynucleotide encoding a GSHE wherein said GSHE is expressed in the transformed fungal cell, and recovering the expressed GSHE. In some embodiments, the filamentous fungal host cell is selected from the group consisting of *Aspergillus, Fusarium, Penicillium* and *Trichoderma*. In further preferred embodiments the fungal host cell is a *Trichoderma* cell, particularly a *T. reesei* cell. In other embodiments, the fungal host cell is an *Aspergillus* cell, particularly an *A. awamori, A. niger* or *A. oryzae* cell. In another embodiment, the promoter is derived from a gene of the filamentous fungal host. In a further embodiment, the polynucleotide encoding the GSHE is derived from a strain of *Humicola grisea* or a strain of *Aspergillus awamori*. In yet another embodiment, the heterologous GSHE produced by the host fungal cell has at least 80% sequence identity with the polypeptide sequence of SEQ ID NO: 3 or with the polypeptide sequence of SEQ ID NO: 6. In other embodiments, the heterologous GSHE produced by the host fungal cell has at least 95% sequence identity with the polypeptide sequence of SEQ ID NO: 3 or with the polypeptide sequence of SEQ ID NO: 6. In further embodiments, the polynucleotide sequence encoding the GSHE has at least 90% sequence identity with the sequence of SEQ ID NO: 1 or SEQ ID NO: 4. In further embodiments, the recombinantly expressed GSHE is encoded by the polynucleotide of SEQ ID NO: 1 or the polynucleotide SEQ ID NO: 4. In another embodiment, the level of glycosylation of the recombinantly expressed GSHE is different from the level of glycosylation of the corresponding native GSHE. In some embodiments, the level of glycosylation of the recombinantly expressed GSHE is less than the level of glycosylation of the corresponding native GSHE. A further embodiment provides enzymatic compositions comprising the GSHE produced according to the method.

In a third aspect, the invention provides a vector comprising a promoter, a granular starch hydrolyzing enzyme (GSHE) signal sequence, a polynucleotide encoding a mature GSHE and a terminator, wherein the promoter and terminator are each functional in a *Trichoderma* cell and are derived from a filamentous fungus and the polynucleotide encoding the GSHE is derived from *Humicola grisea* or *Aspergillus awamori*. In one embodiment, the vector is the plasmid pTrex3g_N13. In a second embodiment the invention provides a *Trichoderma* host cell transformed with the vector.

In a fourth aspect, the invention provides a granular starch hydrolyzing enzyme (GSHE) fraction obtained from a substantially pure culture of *Trichoderma reesei*, wherein the *Trichoderma reesei* comprises a heterologous polynucleotide encoding a GSHE. In one embodiment, the GSHE enzyme fraction includes a GSHE having at least 80% amino acid sequence identity with SEQ ID NO: 3 or a GSHE having at least 80% amino acid sequence identity with SEQ ID NO: 6.

In a fifth aspect, the invention provides, methods for producing a granular starch hydrolyzing enzyme (GSHE) in a *Trichoderma reesei* host cell comprising transforming a *Trichoderma reesei* host cell with a DNA construct, wherein the DNA construct comprises a promoter showing transcriptional activity in *Trichoderma reesei* and which is operably linked to DNA encoding a heterologous GSHE and culturing the transformed *Trichoderma reesei* host cell under suitable culture conditions to allow production of the heterologous GSHE. In one embodiment, the DNA encoding the heterologous GSHE has at least 95% sequence identity with SEQ ID NO: 1 and in other embodiment the DNA encoding the heterologous GSHE has at least 95% sequence identity with SEQ ID NO: 4. In a second embodiment, the method further comprises recovering the GSHE enzyme. In another embodiment, the DNA sequence encoding the heterologous GSHE enzyme is derived from *Humicola grisea* or *Aspergillus awamori*. In some embodiments, the GSHE produced by the transformed *T. reesei* host cell has at least 80% amino acid sequence identity with SEQ ID NO: 3, and in other embodiments the GSHE produced by the transformed *T. reesei* host cell has at least 80% amino acid sequence identity with SEQ ID NO: 6. A further embodiment provides for the *Trichoderma* obtained according to the method.

BRIEF DESCRIPTION OF THE DRAWINGS

FIG. 1 provides the genomic DNA sequence coding for the native *H. grisea* var. *thermoidea* GSHE (SEQ ID NO: 1). The putative introns are in bold and underlined.

FIG. 2A provides the signal sequence and mature amino acid sequence for *H. grisea* var. *thermoidea* GSHE (SEQ ID NO: 2). The putative signal sequence is in bold and underlined.

FIG. 2B provides the mature amino acid sequence for *H. grisea* var. *thermoidea* GSHE (SEQ ID NO: 3).

FIGS. 4A-4E provide the nucleotide sequence (SEQ ID NO: 11) (10738 bp) of the pTrex3g_N13 plasmid of FIG. 3.

FIG. 6 provides the genomic DNA sequence coding for the *Aspergillus awamori* var. *kawachi* GSHE (SEQ ID NO:4). The putative introns are in bold and underlined.

FIG. 7A provides the signal sequence and mature amino acid sequence for *A. awamori* var. *kawachi* GSHE (SEQ ID NO:5). The signal sequence is in bold and underlined.

FIG. 7B provides the mature amino acid sequence for *Aspergillus awamori* var. *kawachi* GSHE (SEQ ID NO:6).

Figures 5, 10:
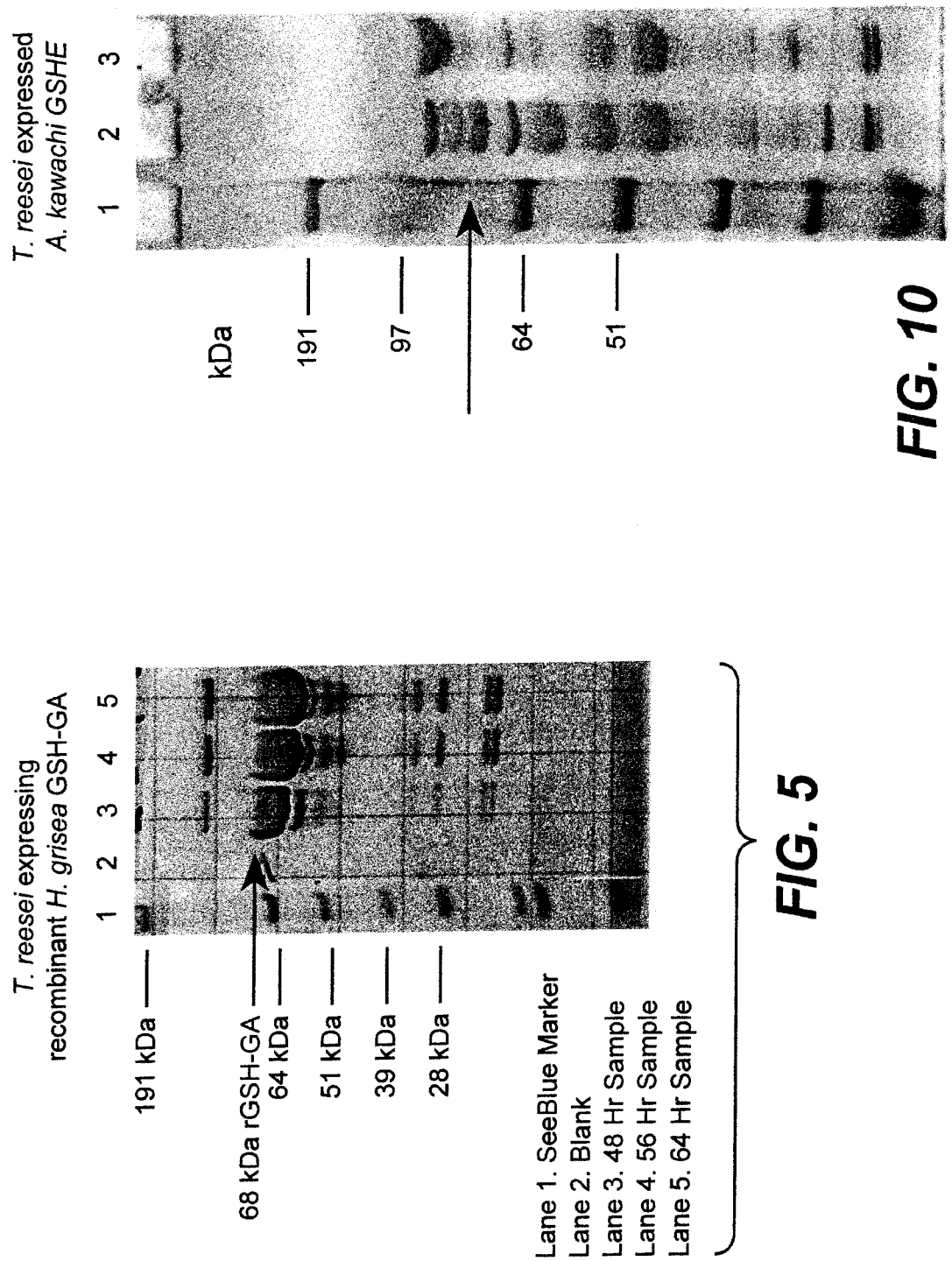
FIG. 5 provides an SDS-PAGE gel indicating the expression of *H. grisea* var. *thermoidea* GSHE in a representative fermentation run for *Trichoderma reesei* clones as described in Example 3. Lane 1 represents the commercial molecular weight marker, SeeBlue (Invitrogen); lane 2 is blank, lane 3 depicts rGSHE expression at 48 hours, lane 4 depicts rGSHE expression at 56 hours and lane 5 depicts rGSHE expression at 64 hours.

FIG. 10 provides an SDS-PAGE gel indicating the expression of *Aspergillus awamori* var. *kawachi* GSHE in a representative fermentation run for *Trichoderma reesei* clones as described in Example 7. Lane 1 represents the commercial molecular weight marker, SeeBlue (Invitrogen); lane 2 depicts rGSHE expression at 162 hours, and lane 3 is a control which depicts the untransformed *Trichoderma reesei* host at 162 hours.

DETAILED DESCRIPTION OF THE INVENTION

In some aspects, the present invention relies on routine techniques and methods used in the field of genetic engineering and molecular biology. The following resources include descriptions of general methodology useful in accordance with the invention: Sambrook et al., MOLECULAR CLONING: A LABORATORY MANUAL (2nd Ed., 1989); Kreigler, GENE TRANSFER AND EXPRESSION; A LABORATORY MANUAL (1990) and Ausubel et al., Eds. CURRENT PROTOCOLS IN MOLECULAR BIOLOGY (1994).

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described.

The invention will now be described in detail by way of reference only using the following definitions and examples. All patents and publications, including all sequences disclosed within such patents and publications, referred to herein are expressly incorporated by reference.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole.

DEFINITIONS

The term "glucoamylase" refers to the amyloglucosidase class of enzymes (e.g., EC.3.2.1.3, glucoamylase, 1,4-alpha-D-glucan glucohydrolase). These are exo-acting enzymes which release glucosyl residues from the non-reducing ends of amylose and amylopectin molecules. The enzyme also hydrolyzes alpha-1,6 and alpha-1,3 linkages although at much slower rates than alpha-1,4 linkages.

The term "granular starch hydrolyzing enzyme (GSHE)" as used herein specifically refers to a glucoprotein which has glucoamylase activity and has the ability to hydrolyze starch in granular form. A preferred GSHE is derived from *Humicola grisea* var. *thermoidea*. Another preferred GSHE is derived from *Aspergillus awamori* var. *kawachi*. In preferred embodiments, the GSHE is expressed in a *Trichoderma* strain, particularly a *T. reesei* strain. In particularly preferred embodiments, GSHE is expressed as an extracellular enzyme.

The term "glycosylation" refers to the post-transcriptional modification of a protein by the addition of carbohydrate moieties, wherein the carbohydrate is either N-linked or O-linked resulting in a glucoprotein. An N-linked carbohydrate moiety of a glycoprotein is attached by a glycosidic bond to the β-amide nitrogen of an asparagine residue. An O-linked carbohydrate is attached by a glycosidic bond to a protein through the hydroxy group of a serine or a threonine residue.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "protein" and "polypeptide" are used interchangeably herein. The conventional one-letter or three-letter code for amino acid residues is used herein.

A "signal sequence" means a sequence of amino acids bound to the N-terminal portion of a protein which facilitates the secretion of the mature form of the protein outside the cell. The definition of a signal sequence is a functional one. The mature form of the extracellular protein lacks the signal sequence which is cleaved off during the secretion process.

The terms "recombinant GSHE", "recombinantly expressed GSHE" and "recombinantly produced GSHE" refer to a mature GSHE protein sequence that is produced in a host cell from a heterologous polynucleotide. The symbol "r" may be used to denote "recombinant". The protein sequence of a rGSHE excludes a signal sequence.

The terms "native GSHE" and "nGSHE" refer to a GSHE that is derived from a microbial host other than the fungal host for which recombinant GSHE expression is desired. In preferred embodiments, a native GSHE is derived from a *Humicola grisea* strain or an *Aspergillus awamori* strain.

A "gene" refers to a DNA segment that is involved in producing a polypeptide and includes regions preceding and following the coding regions as well as intervening sequences (introns) between individual coding segments (exons).

The term "nucleic acid" encompasses DNA, RNA, single stranded or double stranded and chemical modifications thereof. The terms "nucleic acid" and "polynucleotide" may be used interchangeably herein. Because the genetic code is degenerate, more than one codon may be used to encode a particular amino acid, and the present invention encompasses polynucleotides which encode a particular amino acid sequence.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" as used herein means a DNA construct comprising a DNA sequence which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

A "promoter" is a regulatory sequence that is involved in binding RNA polymerase to initiate transcription of a gene. The promoter may be an inducible promoter or a constitutive promoter. A preferred promoter used in the invention is *Trichoderma reesei* cbh1, which is an inducible promoter.

"Under transcriptional control" is a term well understood in the art that indicates that transcription of a polynucleotide sequence, usually a DNA sequence, depends on its being operably linked to an element which contributes to the initiation of, or promotes transcription.

"Under translational control" is a term well understood in the art that indicates a regulatory process which occurs after mRNA has been formed.

As used herein when describing proteins and genes that encode them, the term for the gene is not capitalized and is italicized, (e.g., the gene that encodes the *Humicola grisea* GSHE may be denoted as gla1). The term for the protein is generally not italicized and the first letter is capitalized, (e.g., the protein encoded by the gla1 gene may be denoted as Gla1).

The term "operably linked" refers to juxtaposition wherein the elements are in an arrangement allowing them to be functionally related. For example, a promoter is operably linked to a coding sequence if it controls the transcription of the sequence.

The term "selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

The term "derived" encompasses the terms "originated from", "obtained" or "obtainable from", and "isolated from".

"Host strain" or "host cell" means a suitable host for an expression vector or DNA construct comprising a polynucleotide encoding a GSHE according to the invention. Specifically, host strains are preferably filamentous fungal cells. In a preferred embodiment of the invention, "host cell" means both the cells and protoplasts created from the cells of a filamentous fungal strain and particularly a *Trichoderma* sp. or an *Aspergillus* sp.

The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic. In the present invention, the filamentous fungal parent cell may be a cell of a species of, but not limited to, *Trichoderma*, (e.g., *Trichoderma reesei* (previously classified as *T. longibrachiatum* and currently also known as *Hypocrea jecorina*), *Trichoderma viride, Trichoderma koningii, Trichoderma harzianum*); *Penicillium* sp., *Humicola* sp. (e.g., *Humicola insolens* and *Humicola grisea*); *Chrysosporium* sp. (e.g., *C. lucknowense*), *Gliocladium* sp., *Aspergillus* sp. (e.g., *A. oryzae, A. niger*, and *A. awamori*), *Fusarium* sp., *Neurospora* sp., *Hypocrea* sp., and *Emericella* sp. (See also, Innis et al., (1985) *Sci.* 228:21-26).

As used herein, the term "*Trichoderma*" or "*Trichoderma* sp." refer to any fungal genus previously or currently classified as *Trichoderma*.

The term "culturing" refers to growing a population of microbial cells under suitable conditions in a liquid or solid medium.

The term "heterologous" with reference to a polynucleotide or protein refers to a polynucleotide or protein that does not naturally occur in a host cell. In some embodiments, the protein is a commercially important industrial protein. It is intended that the term encompass proteins that are encoded by naturally occurring genes, mutated genes, and/or synthetic genes. The term "homologous" with reference to a polynucleotide or protein refers to a polynucleotide or protein that occurs naturally in the host cell.

The terms "recovered", "isolated", and "separated" as used herein refer to a protein, cell, nucleic acid or amino acid that is removed from at least one component with which it is naturally associated.

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein the term "specific activity" means an enzyme unit defined as the number of moles of substrate converted to product by an enzyme preparation per unit time under specific conditions. Specific activity is expressed as units (U)/mg of protein.

As used herein the term "enzyme unit" refers to the amount of enzyme that converts 1 micromole of substrate per minute to the substrate product at optimum assay conditions. For example, in one embodiment, the term "glucoamylase activity unit" (GAU) is defined as the amount of enzyme required to produce 1 micromole of glucose per minute under assay conditions of, for example 40° C. and pH 5.0. In another embodiment, a granular starch hydrolyzing enzyme unit (GSHE U) is defined as being the amount of GSHE required to produce 1 g of glucose per minute from granular starch under assay conditions of, for example 25° C. at pH 5.0. In another embodiment a GSHE U is defined as being the amount of GSHE required to produce 1 mg of glucose per minute from granular starch under assay conditions, of 50° C. at pH 4.5.

As used herein the term "starch" refers to any material comprised of the complex polysaccharide carbohydrates of plants, comprised of amylose and amylopectin with the formula $(C_6H_{10}O_5)_x$, wherein X can be any number. In particular, the term refers to any plant-based material including but not limited to grains, grasses, tubers and roots and more specifically to the plants wheat, barley, corn, rye, rice, sorghum, brans, cassava, millet, potato, sweet potato, and tapioca.

The term "granular starch" refers to raw uncooked starch, e.g., granular starch that has not been subject to gelatinization.

The term "starch-liquefying enzyme" refers to an enzyme that effects the fluidization of granular starch. Exemplary starch liquefying enzymes include alpha amylases (e.g., E.C. 3.2.1.1).

The term "alpha-amylase (e.g., E.C. class 3.2.1.1)" refers to enzymes that catalyze the hydrolysis of alpha-1,4-glucosidic linkages. These enzymes have also been described as those effecting the exo or endohydrolysis of 1,4-α-D-glucosidic linkages in polysaccharides containing 1,4-α-linked D-glucose units. Another term used to describe these enzymes is "glycogenase". Exemplary enzymes include alpha-1,4-glucan 4-glucanohydrase glucanohydrolase.

"ATCC" refers to American Type Culture Collection located at Manassas, Va. 20108 (ATCC; www.atcc.org).

"NRRL" refers to the Agricultural Research Service Culture Collection, National Center for Agricultural Utilization Research (and previously known as USDA Northern Regional Research Laboratory), Peoria, Ill.

"A", "an" and "the" include plural references unless the context clearly dictates otherwise.

As used herein the term "comprising" and its cognates are used in their inclusive sense; that is, equivalent to the term "including" and its corresponding cognates.

PREFERRED EMBODIMENTS

Host Organisms

The present invention provides host cells, which can express a heterologous polynucleotide encoding a GSHE. The host cell is preferably a filamentous fungal cell. In a preferred embodiment, the filamentous fungal host is a strain of *Aspergillus* sp, *Trichoderma* sp, *Fusarium* sp and *Penicillium* sp. Particularly preferred fungal host cells include *A. nidulans, A. awamori, A. oryzae, A. aculeatus, A. niger, A. japonicus, T. reesei, T. viride, F. oxysporum*, and *F. solani*. *Aspergillus* strains are disclosed in Ward et al. (1993) *Appl. Microbiol. Biotechnol.* 39:738-743 and Goedegebuur et al., (2002) *Curr Gene* 41:89-98. In a most preferred embodiment, the host is a strain of *Trichoderma* and particularly a strain of *T. reesei*. Strains of *T. reesei* are known and nonlimiting examples include ATCC No. 13631, ATCC No. 26921, ATCC No. 56764, ATCC No. 56765, ATCC No. 56767 and NRRL 15709. In some preferred embodiments, the host strain is a derivative of RL-P37. RL-P37 is disclosed in Sheir-Neiss et al. (1984) *Appl. Microbiol. Biotechnology* 20:46-53.

The host strain may be previously manipulated through genetic engineering. In some embodiments, various native genes of the fungal host cell have been inactivated. These genes include, for example genes encoding cellulolytic enzymes, such as endoglucanases (EG) and exocellobiohydrolases (CBH) (e.g. cbh1, cbh2, egl1 and egl3). U.S. Pat. No. 5,650,322 discloses derivative strains of RL-P37 having deletions in the cbh1 gene and the cbh2 gene.

B. Glucoamylases and Granular Starch Hydrolyzing Enzymes

In the context of this invention, a glucoamylase (E.C. 3.2.1.3) is an enzyme that removes successive glucose units from the non-reducing ends of starch. The enzyme can hydrolyze both linear and branched glucosidic linkages of starch, amylose and amylopectin. While glucoamylase may be derived from bacteria, plants and fungi, preferred glucoamylases encompassed by the present invention are derived from fungal strains. Glucoamylases secreted from fungi of the genera *Aspergillus, Rhizopus, Humicola* and *Mucor* have been derived from various fungal strains, including *Aspergillus niger, Aspergillus awamori, Rhizopus niveus, Rhizopus oryzae, Mucor miehe, Humicola grisea, Aspergillus shirousami* and *Humicola (Thermomyces) laniginosa* (See, Boel et al., (1984) *EMBO J.* 3:1097-1102; WO 92/00381; WO 00/04136; Chen et al., (1996) *Prot. Eng.* 9:499-505; Taylor et al., (1978) *Carbohydrate Res.* 61:301-308 and Jensen et al., (1988) *Can. J. Microbiol.* 34:218-223).

A particular group of enzymes having glucoamylase activity are known as granular starch hydrolyzing enzyme(s) GSHE (See e.g., Tosi et al., (1993) *Can. J. Microbiol.* 39:846-855). GSHEs not only have glucoamylase activity, but also are able to hydrolyze granular (raw) starch. GSHEs have been recovered from fungal cells such as *Humicola* sp., *Aspergillus* sp. and *Rhizopus* sp. A *Rhizopus oryzae* GSHE has been described in Ashikari et al., (1986) *Agric. Biol. Chem.* 50:957-964 and U.S. Pat. No. 4,863,864. A *Humicola grisea* GSHE is described by Allison et al., (1992) *Curr. Genet.* 21:225-229 and European Patent No. 171218. The gene encoding this enzyme is also known in the art as "gla1". An *Aspergillus awamori* var. *kawachi* GSHE is described by Hayashida et al., (1989) *Agric. Biol. Chem.* 53:923-929. An *Aspergillus shirousami* GSHE is described by Shibuya et al., (1990) *Agric. Biol. Chem.* 54:1905-1914.

In one embodiment, a GSHE may be derived from a strain of *Humicola* grisea, particularly a strain of *H. grisea* var. *thermoidea* (See, U.S. Pat. No. 4,618,579).

In some preferred embodiments, the *Humicola grisea* GSHE is recovered from fungi including ATCC 16453, NRRL (USDA Northern Regional Research Laboratory, Peoria, Ill.) 15219, NRRL 15220, NRRL 15221, NRRL 15222, NRRL 15223, NRRL 15224 and NRRL 15225, as well as genetically altered strains thereof. These species produce enzymatic glucoamylase preparations that are immunologically the same (See, EP 0 171 218).

In one embodiment, a GSHE may be derived from a strain of *Aspergillus awamori* particularly a strain of *A. awamori* var. *kawachi*. (For example see, Hayashida, et al. (1989) *Agric. Biol. Chem.* 53:923-929).

In another embodiment, GSHEs exhibit a maximum pH activity within a pH range of 4 to 7.5 and also within the pH range of 5 to 7.5 and maximum activity in the temperature range of 50° C. to 60° C.

In another particularly preferred embodiment, the GSHE is a GSHE comprising an amino acid sequence having at least 50%, 55%, 60%, 65%, 70%, 75%, 80%, 85%, 90%, 93%, 95%, 97%, 98% and 99% sequence identity with the amino acid sequence set forth in SEQ ID NO:3. In another embodiment, the GSHE comprises an amino acid sequence having at least 80% sequence identity with SEQ ID NO:3. In a further embodiment, the GSHE comprises an amino acid sequence having at least 90% sequence identity to SEQ ID NO:3. The GSHE may also comprises an amino acid sequence having at least 95% sequence identity with SEQ ID NO:3. In a further embodiment, the GSHE comprises the amino acid sequence of SEQ ID NO:3.

In other embodiments, the GSHE comprising the amino acid sequence of SEQ ID NO:3 or an amino acid sequence having at least 80% sequence identity with SEQ ID NO:3 is encoded by a polynucleotide having at least 70%, 80%, 85%, 90%, 93%, 95%, 97%, 98% and 99% sequence identity to the sequence of SEQ ID NO:1. In a preferred embodiment, the GSHE having an amino acid sequence of SEQ ID NO:3 is encoded by a polynucleotide having at least 70%, 80%, 85%, 90%, 93%, 95%, 97%, 98% and 99% sequence identity with SEQ ID NO:1. In a particularly preferred embodiment, the nucleic acid sequence encoding the GSHE of SEQ ID NO:3 is the nucleic acid sequence of SEQ ID NO:1.

In another particularly preferred embodiment, the GSHE is a GSHE comprising an amino acid sequence having at least 50%, 55%, 60%, 65%, 70%, 75%, 80%, 85%, 90%, 93%, 95%, 97%, 98% and 99% sequence identity with the amino acid sequence set forth in SEQ ID NO:6. In another embodiment, the GSHE comprises an amino acid sequence having at least 80% sequence identity with SEQ ID NO:6. In a further embodiment, the GSHE comprises an amino acid sequence having at least 90% sequence identity with SEQ ID NO:6. The GSHE may also comprises an amino acid sequence having at least 95% sequence identity with SEQ ID NO:6. In a further embodiment, the GSHE comprises the sequence of SEQ ID NO:6.

In other embodiments, the GSHE enzyme comprising the amino acid sequence of SEQ ID NO:6 or an amino acid sequence having at least 80% sequence identity with SEQ ID NO:6 is encoded by a polynucleotide having at least 70%, 80%, 85%, 90%, 93%, 95%, 97%, 98% and 99% sequence identity with the sequence of SEQ ID NO:4. In a preferred embodiment, the GSHE having an amino acid sequence of SEQ ID NO:6 is encoded by a polynucleotide having at least 70%, 80%, 85%, 90%, 93%, 95%, 97%, 98% and 99% sequence identity to SEQ ID NO:3. In a particularly preferred embodiment, the nucleic acid sequence encoding the GSHE of SEQ ID NO:6 is the nucleic acid sequence of SEQ ID NO:4.

A polynucleotide or a polypeptide having a certain percent (e.g. 80%, 85%, 90%, 95%, or 99%) of sequence identity with another sequence means that, when aligned, that percentage of bases or amino acid residues are the same in comparing the two sequences. This alignment and the percent homology or identity can be determined using any suitable software program known in the art, for example those described in CURRENT PROTOCOLS IN MOLECULAR BIOLOGY (F. M. Ausubel et al. (eds) 1987, Supplement 30, section 7.7.18). Preferred programs include the GCG Pileup program, FASTA (Pearson et al. (1988) *Proc. Natl, Acad. Sci. USA* 85:2444-2448), and BLAST (BLAST Manual, Altschul et al., Natl. Cent. Biotechnol. Inf., Natl Lib. Med. (NCIB NLM NIH), Bethesda, Md., and Altschul et al., (1997) *NAR* 25:3389-3402). Another preferred alignment program is ALIGN Plus (Scientific and Educational Software, PA), preferably using default parameters. Another sequence software program that finds use is the TFASTA Data Searching Program available in the Sequence Software Package Version 6.0 (Genetics Computer Group, University of Wisconsin, Madison, Wis.).

One skilled in the art will recognize that sequences encompassed by the invention are also defined by the ability to hybridize under stringent hybridization conditions with the exemplified GSHE sequences (e.g., SEQ ID NO:1 or SEQ ID NO:4). A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (See, e.g., Sambrook (1989) supra, particularly chapters 9 and 11). In some embodiments, stringent conditions correspond to a Tm of 65° C. and 0.1×SSC, 0.1% SDS.

In some embodiments of the present invention, a GSHE is produced as an extracellular enzyme by a filamentous fungal cell and particularly by a *Trichoderma* host that has been genetically engineered to comprise a heterologous polynucleotide encoding a GSHE derived from a *Humicola* sp. In preferred embodiments, the GSHE is derived from a strain of *Humicola grisea*, and in some particularly preferred embodiments, the GSHE is derived from a strain of *Humicola grisea* var. *thermoidea*.

In one embodiment encompassed by the invention, the GSHE produced by the *Trichoderma* host (rGSHE) has at least 50%, 55%, 60%, 65%, 70%, 75%, 80%, 85%, 90%, 93%, 95%, 97%, 98% or 99% sequence identity with the amino acid sequence set forth in SEQ ID NO:3. In another embodiment, a *Trichoderma* host, is transformed with a heterologous polynucleotide encoding a GSHE having at least 80% sequence identity with SEQ ID NO:3. In a further embodiment, a *Trichoderma* host, is transformed with a heterologous polynucleotide encoding a GSHE having at least 90% sequence identity with SEQ ID NO:3. In another embodiment, a *Trichoderma* host, is transformed with a heterologous polynucleotide encoding a GSHE having at least 95% sequence identity to SEQ ID NO:3. In other embodiments, the polynucleotide encoding the GSHE has at least 80% sequence identity with SEQ ID NO:1 and preferably at least 95% sequence identity with SEQ ID NO:1. In a particularly preferred embodiment, the rGSHE is expressed in a *Trichoderma reesei* strain and has at least 80% sequence identity with the amino acid sequence of SEQ ID NO:3.

In another preferred embodiment of the invention, the GSHE is produced as an extracellular enzyme by a filamentous fungal cell and particularly by a *Trichoderma* host that has been genetically engineered to comprise a polynucleotide encoding a GSHE derived from *Aspergillus* sp. In some embodiments, the GSHE derived from a strain of *Aspergillus awamori*, and in some particularly preferred embodiments, the GSHE is derived from a strain of *Aspergillus awamori* var. *kawachi*.

In one embodiment, the GSHE produced by the *Trichoderma* host (rGSHE) has at least 50%, 55%, 60%, 65%, 70%, 75%, 80%, 85%, 90%, 93%, 95%, 97%, 98% or 99% sequence identity with the amino acid sequence set forth in SEQ ID NO:6. In another embodiment, a *Trichoderma* host is transformed with a heterologous polynucleotide encoding a GSHE having at least 80% sequence identity with SEQ ID NO:6. In a further embodiment, a *Trichoderma* host is transformed with a heterologous polynucleotide encoding a GSHE having at least 90% sequence identity to SEQ ID NO:6. In another embodiment, a *Trichoderma* host is be transformed with a heterologous polynucleotide encoding a GSHE having at least 95% sequence identity with SEQ ID NO:6. In other embodiments, the polynucleotide encoding the GSHE will have at least 90% sequence identity with SEQ ID NO:4 and preferably at least 95% sequence identity with SEQ ID NO:4. In a particularly preferred embodiment, the GSHE is expressed in a *Trichoderma reesei* strain and has at least 80% sequence identity with the sequence of SEQ ID NO:6.

In some embodiments, the level of glycosylation of a recombinantly expressed GSHE is different than the level of glycosylation of the corresponding native GSHE (e.g., GSHE which was originally derived from *Humicola grisea* or *Aspergillus awamori* has a different level of glycosylation than the level of glycosylation of the produced recombinant GSHE). In one embodiment, the level of glycosylation is different even if the rGSHE has at least 80% amino acid sequence identity to the native GSHE derived from *Humicola grisea* or *Aspergillus awamori*. More specifically, in some embodiments, a rGSHE expressed in *Trichoderma* and particularly a strain of *T. reesei* has a different level of glycosylation than the level of glycosylation from the corresponding nGSHE. In other embodiments, the level of glycosylation is higher, while in other embodiments the level of glycosylation is lower.

In one embodiment, the level of glycosylation of the recombinantly expressed GSHE is lower than the level of a corresponding native GSHE. For example, the level of glycosylation for rGSHE may be at least 1%, 5%, 10%, 15%, 20%, 25%, 30%, 35%, 40%, 45% 50%, 55%, 60%, or 65% less than the level of glycosylation of the corresponding nGSHE. In some embodiments, the level of glycosylation in a rGSHE according to the invention is at least 25% less than the level of glycosylation of a corresponding nGSHE. In other embodiments, the level of glycosylation of rGSHE expressed by a host may be at least 1%, 5%, 10%, 15%, 20%, 25%, 30%, 35%, 40% 50%, 60% 70%, 80%, 100%, 125%, 150%, 175%, 200%, 225% or 250% greater than the level of a corresponding native form of GSHE. In some embodiments, the level of glycosylation of rGSHE expressed by a host is at least 100% greater that the level of nGSHE.

In another embodiment, the recombinantly produced GSHE encompassed by the invention has greater stability at lower pH levels than a corresponding native GSHE at optimum temperature levels. More specifically, in some embodiments, a rGSHE expressed in *Trichoderma*, which was originally derived from *Humicola grisea* var. *thermoidea*, has greater stability at pH levels of 3.5 to 4.0 compared to a corresponding native GSHE at temperatures of 45-55° C. For example, in one embodiment, at a pH level about 3.5 the stability of rGSHE, and particularly *Humicola grisea* var. *thermoidea* GSHE expressed in *Trichoderma reesei*, is more than double the level of stability of nGSHE from *Humicola grisea* var. *thermoidea*.

C. Vectors

According to the invention, a DNA construct comprising nucleic acid encoding a GSHE encompassed by the invention is constructed to transfer GSHE into a host cell. Thus, GSHE which can be expressed in enzyme form may be introduced into a host cell using a vector, particularly an expression vector which comprises regulatory sequences operably linked to a GSHE coding sequence.

The vector may be any vector which when introduced into a fungal host cell is integrated into the host cell genome and is replicated. Reference is made to the Fungal Genetics Stock Center Catalogue of Strains (FGSC, <www.fgsc.net>) for a list of vectors. Additional examples of suitable expression and/or integration vectors are provided in Sambrook et al., (1989) supra, and Ausubel (1987) supra, and van den Hondel et al. (1991) in Bennett and Lasure (Eds.) MORE GENE MANIPULATIONS IN FUNGI, Academic Press pp. 396-428 and U.S. Pat. No. 5,874,276. Particularly useful vectors include pFB6, pBR322, PUC18, pUC100 and pENTR/D.

In preferred embodiments, nucleic acid encoding a GSHE encompassed by the invention is operably linked to a suitable promoter, which shows transcriptional activity in the fungal host cell. The promoter may be derived from genes encoding proteins either homologous or heterologous to the host cell. Preferably, the promoter is useful in a *Trichoderma* host. Suitable nonlimiting examples of promoters include cbh1, cbh2, egl1, egl2. In one embodiment, the promoter is one that is native to the host cell. For example, when *T. reesei* is the host, the promoter is a native *T. reesei* promoter. In a preferred embodiment, the promoter is *T. reesei* cbh1, which is an inducible promoter and has been deposited in GenBank under Accession No. D86235. An "inducible promoter" is a promoter that is active under environmental or developmental regulation. In another embodiment, the promoter is one that is heterologous to the fungal host cell. Other examples of useful promoters include promoters from *A. awamori* and *A. niger* glucoamylase genes (See, Nunberg et al., (1984) *Mol. Cell. Biol.* 4:2306-2315 and Boel et al., (1984) *EMBO J.* 3:1581-1585). Also, the promoters of the *T. reesei* xln1 gene and the cellobiohydrolase 1 gene may be useful (EPA 137280A1).

Figures 2A, 2B:
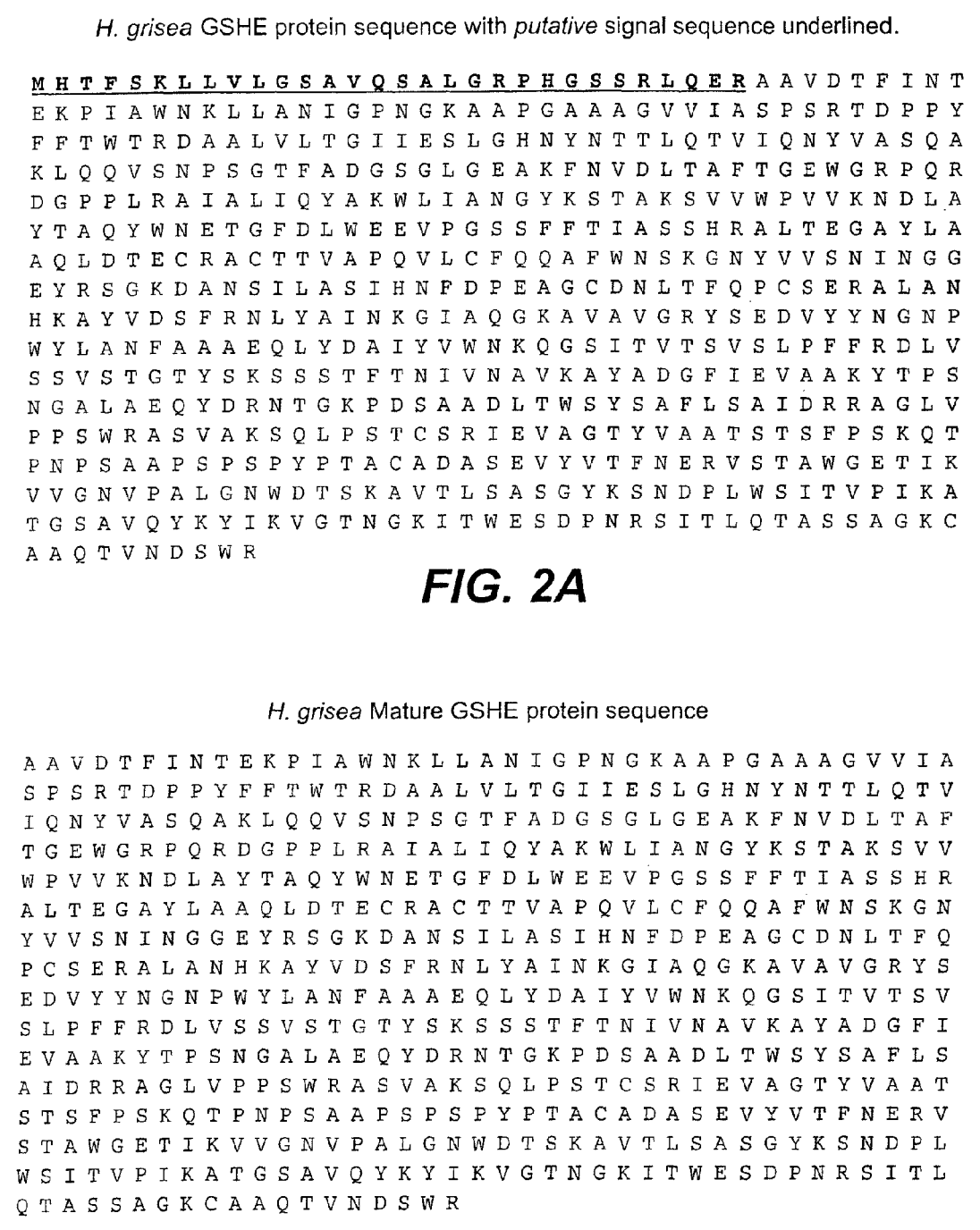

In some preferred embodiments, the GSHE coding sequence is operably linked to a signal sequence. The DNA encoding the signal sequence is preferably that which is naturally associated with the GSHE gene to be expressed. Preferably, the signal sequence is en coded by a *Humicola grisea* or *Aspergillus awamori* gene which encodes a GSHE. More preferably the signal sequence has at least 90%, at least 95%, at least 97%, and at least 99% sequence identity to the signal sequence of depicted in FIGS. 2A and 7A. In additional embodiments, a signal sequence and a promoter sequence comprising a DNA construct or vector to be introduced into a fungal host cell are derived from the same source. For example, in some embodiments, the signal sequence is the cdh1 signal sequence which is operably linked to a cdh1 promoter.

In some embodiments, the expression vector also includes a termination sequence. In one embodiment, the termination sequence and the promoter sequence are derived from the same source. In another embodiment, the termination sequence is homologous to the host cell. A particularly suitable terminator sequence is cbh1 derived from a *Trichoderma* strain and particularly *T. reesei*. Other useful fungal terminators include the terminator from *A. niger* or *A. awamori* glucoamylase gene (Nunberg et al. (1984) supra, and Boel et al., (1984) supra).

In some embodiments, an expression vector includes a selectable marker. Examples of preferred selectable markers include ones which confer antimicrobial resistance (e.g., hygromycin and phleomycin). Nutritional selective markers also find use in the present invention including those markers known in the art as amdS argB and pyr4. Markers useful in vector systems for transformation of *Trichoderma* are known in the art (See, e.g., Finkelstein, chapter 6 in BIOTECHNOLOGY OF FILAMENTOUS FUNGI, Finkelstein et al. Eds. Butterworth-Heinemann, Boston, Mass. (1992), Chap. 6.; and Kinghorn et al. (1992) APPLIED MOLECULAR GENETICS OF FILAMENTOUS FUNGI, Blackie Academic and Professional, Chapman and Hall, London). In a preferred embodiment, the selective marker is the amdS gene, which encodes the enzyme acetamidase, allowing transformed cells to grow on acetamide as a nitrogen source. The use of *A. nidulans* amdS gene as a selective marker is described in Kelley et al., (1985) *EMBO J.* 4:475-479 and Penttila et al., (1987) *Gene* 61:155-164.

An expression vector comprising a DNA construct with a polynucleotide encoding a GSHE may be any vector which is capable of replicating autonomously in a given fungal host organism or of integrating into the DNA of the host. In some embodiments, the expression vector is a plasmid. In preferred embodiments, two types of expression vectors for obtaining expression of genes are contemplated.

The first expression vector comprises DNA sequences in which the promoter, GSHE-coding region, and terminator all originate from the gene to be expressed. In some embodiments, gene truncation is obtained by deleting undesired DNA sequences (e.g., DNA encoding unwanted domains) to leave the domain to be expressed under control of its own transcriptional and translational regulatory sequences.

The second type of expression vector is preassembled and contains sequences required for high-level transcription and a selectable marker. In some embodiments, the coding region for a GSHE gene or part thereof is inserted into this general-purpose expression vector such that it is under the transcriptional control of the expression construct promoter and terminator sequences. In some embodiments, genes or part thereof are inserted downstream of a strong promoter, such as the strong cbh1 promoter.

Methods used to ligate the DNA construct comprising a polynucleotide encoding a GSHE, a promoter, a terminator and other sequences and to insert them into a suitable vector are well known in the art. Linking is generally accomplished by ligation at convenient restriction sites. If such sites do not exist, the synthetic oligonucleotide linkers are used in accordance with conventional practice. (See, Sambrook (1989) supra, and Bennett and Lasure, MORE GENE MANIPULATIONS IN FUNGI, Academic Press, San Diego (1991) pp 70-76). Additionally, vectors can be constructed using known recombination techniques (e.g., Invitrogen Life Technologies, Gateway Technology).

Where it is desired to obtain a fungal host cell having one or more inactivated genes known methods may be used (e.g. methods disclosed in U.S. Pat. No. 5,246,853, U.S. Pat. No. 5,475,101 and WO92/06209). Gene inactivation may be accomplished by complete or partial deletion, by insertional inactivation or by any other means which renders a gene nonfunctional for its intended purpose (such that the gene is prevented from expression of a functional protein). Any gene from a *Trichoderma* sp or other filamentous fungal host, which has been cloned can be deleted, for example cbh1, cbh2, egl1 and egl2 genes. In some embodiments, gene deletion may be accomplished by inserting a form of the desired gene to be inactivated into a plasmid by methods known in the art. The deletion plasmid is then cut at an appropriate restriction enzyme site(s), internal to the desired gene coding region, and the gene coding sequence or part thereof is replaced with a selectable marker. Flanking DNA sequences from the locus of the gene to be deleted (preferably between about 0.5 to 2.0 kb) remain on either side of the marker gene. An appropriate deletion plasmid will generally have unique restriction enzyme sites present therein to enable the fragment containing the deleted gene, including the flanking DNA sequences and the selectable markers gene to be removed as a single linear piece.

D. Transformation of Host Cells

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (See, e.g., Ausubel et al., (1987), supra, chapter 9; and Sambrook (1989) supra, and Campbell et al., (1989) *Curr. Genet.* 16:53-56). The expression of heterologous protein in *Trichoderma* is described in U.S. Pat. No. 6,022,725; U.S. Pat. No. 6,268,328; Harkki et al. (1991); *Enzyme Microb. Technol.* 13:227-233; Harkki et al., (1989) *Bio Technol.* 7:596-603; EP 244,234; EP 215,594; and Nevalainen et al., "*The Molecular Biology of Trichoderma and its Application to the Expression of Both Homologous and Heterologous Genes*", in MOLECULAR INDUSTRIAL MYCOLOGY, Eds. Leong and Berka, Marcel Dekker Inc., NY (1992) pp. 129-148). Reference is also made to Cao et al., (2000) *Sci.* 9:991-1001 for transformation of *Aspergillus* strains.

Preferably, genetically stable transformants are constructed with vector systems whereby the nucleic acid encoding GSHE is stably integrated into a host strain chromosome. Transformants are then purified by known techniques.

In one nonlimiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium (i.e., medium that lacks acetamide), harvesting spores from this culture medium and determining the percentage of these spores which subsequently germinate and grow on selective medium containing acetamide. Alternatively, other methods known in the art may be used to select transformants.

In one specific embodiment, the preparation of *Trichoderma* sp. for transformation involves the preparation of protoplasts from fungal mycelia. (See, Campbell et al., (1989) *Curr. Genet.* 16:53-56). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of DNA into the host *Trichoderma* sp. strain is dependent upon the calcium ion concentration. Generally, between about 10 mM $CaCl_2$ and 50 mM $CaCl_2$ is used in an uptake solution. Besides the need for the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes, thus permitting the contents of the medium to be delivered into the cytoplasm of the *Trichoderma* sp. strain and the plasmid DNA is transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL, preferably $2 \times 10^6$/mL are used in transformation. A volume of 100 μL of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation. Similar procedures are available for other fungal host cells. (See, e.g., U.S. Pat. Nos. 6,022,725 and 6,268,328, both of which are incorporated by reference).

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated either at room temperature or on ice before the addition of a sorbitol and $CaCl_2$ solution. The protoplast suspension is then further added to molten aliquots of a growth medium. This growth medium permits the growth of transformants only.

E. Cell Culture

Generally, cells are cultured in a standard medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth also find use in the present invention.

Culture conditions are also standard, (e.g., cultures are incubated at approximately 28° C. in appropriate medium in shake cultures or fermenters until desired levels of GSHE expression are achieved). Preferred culture conditions for a given filamentous fungus are known in the art and may be found in the scientific literature and/or from the source of the fungi such as the American Type Culture Collection and Fungal Genetics Stock Center.

After fungal growth has been established, the cells are exposed to conditions effective to cause or permit the expression of a GSHE and particularly a GSHE as defined herein. In cases where a GSHE coding sequence is under the control of an inducible promoter, the inducing agent (e.g., a sugar, metal salt or antimicrobial), is added to the medium at a concentration effective to induce GSHE expression.

F. Identification of GSHE Activity

In some embodiments, in order to evaluate the expression of a GSHE by a cell line that has been transformed with a heterologous polynucleotide encoding a GSHE encompassed by the invention, assays are carried out at the protein level, the RNA level and/or by use of functional bioassays particular to glucoamylase activity and/or production.

In general, assays employed to analyze the expression of a GSHE include Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of a GSHE may be measured in a sample directly, for example, by assays directly measuring reducing sugars such as glucose in the culture medium and by assays for measuring glucoamylase activity, expression and/or production. Substrates useful for assaying GSHE activity include granular starch substrates, including but not limited to corn, wheat, rice, barley, tapioca, potato, and cassava. For example, in some embodiments, glucose concentration is determined by any convenient method such as by using glucose reagent kit No 15-UV (Sigma Chemical Co.) or an instrument such as Technicon Autoanalyzer. In addition glucose oxidase kits and glucose hexose kits are commercially available from Instrumentation Lab. (Lexington, Mass.). Glucoamylase activity may be assayed by the 3,5-dinitrosalicylic acid (DNS) method (See, Goto et al., (1994) Biosci. Biotechnol. Biochem. 58:49-54). In one nonlimiting example, a rGSHE has the ability to hydrolyze granular starch in a 15% starch solids suspension in water to a solution of saccharides of at least 90%, 95% and/or 97% wt glucose on a dry substance basis.

In some embodiments of the invention, the GSHE expressed by a recombinant *Trichoderma* host is greater than 0.5 gram protein per liter (g/L) of culture medium. In some embodiments, the amount of GSHE expressed by a recombinant *Trichoderma* host is greater than 1 g/L of culture media. In some embodiments, the amount of GSHE expressed by a recombinant *Trichoderma* host is greater than 2 g/L of culture media. In other embodiments, the amount of GSHE expressed by a recombinant *Trichoderma* host is greater than 5 g/L of culture media. Yet in other embodiments, the amount of GSHE expressed by a recombinant *Trichoderma* host is greater than 10 g/L of culture medium. The amount of expressed GSHE in some instances is greater than 20 g/L, greater than 25 g/L, greater than 30 g/L and greater than 50 g/L of culture media.

In additional embodiments, protein expression, is evaluated by immunological methods, such as immunohistochemical staining of cells, tissue sections or immunoassay of tissue culture medium, (e.g., by Western blot or ELISA). Such immunoassays can be used to qualitatively and quantitatively evaluate expression of a GSHE. The details of such methods are known to those of skill in the art and many reagents for practicing such methods are commercially available. Exemplary assays include ELISA, competitive immunoassays, radioimmunoassays, Western blot, immunofluorescent assays and the like. In general, commercially available antibodies and/or kits may be used for the quantitative immunoassay of the expression level of a GSHE.

G. Methods for Purifying GSHE

In general, a GSHE produced in cell culture is secreted into the medium and may be purified or isolated, (e.g., by removing unwanted components from the cell culture medium). In some cases, a GSHE is produced in a cellular form, necessitating recovery from a cell lysate. In such cases, the enzyme is purified from the cells in which it was produced using techniques routinely employed by those of skill in the art. Examples of these techniques include, but are not limited to, affinity chromatography (Tilbeurgh et al., (1984) *FEBS Lett.* 16:215), ion-exchange chromatographic methods (Goyal et al., (1991) *Biores. Technol.* 36:37; Fliess et al., (1983) *Eur. J. Appl. Microbiol. Biotechnol.* 17:314; Bhikhabhai et al., (1984) *J. Appl. Biochem.* 6:336; and Ellouz et al., (1987) *Chromatography* 396:307), including ion-exchange using materials with high resolution power (Medve et al., (1998) *J. Chromatography A* 808:153), hydrophobic interaction chromatography (See, Tomaz and Queiroz, (1999) *J. Chromatography A* 865:123; two-phase partitioning (See, Brumbauer, et al., (1999) *Bioseparation* 7:287); ethanol precipitation; reverse phase HPLC, chromatography on silica or on a cation-exchange resin such as DEAE, chromatofocusing, SDS-PAGE, ammonium sulfate precipitation, and gel filtration (e.g., Sephadex G-75). The degree of purification desired will vary depending on the use of the GSHE. In some embodiments of the present invention, purification will not be necessary.

H. Industrial Uses of the rGSHE—Fermentations

In some embodiments of the present invention, fungal cells expressing a heterologous GSHE are grown under batch or continuous fermentation conditions. A classical batch fermentation is a closed system, wherein the composition of the medium is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase and finally to a stationary phase where growth rate is diminished or halted. If untreated, cells in the stationary phase eventually die. In general, cells in log phase are responsible for the bulk of production of end product.

A variation on the standard batch system is the "fed-batch fermentation" system, which also finds use with the present invention. In this variation of a typical batch system, the substrate is added in increments as the fermentation progresses. Fed-batch systems are useful when catabolite repression is apt to inhibit the metabolism of the cells and where it is desirable to have limited amounts of substrate in the medium. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate an all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology.

There are a wide variety of industrial uses for the recombinant GSHE produced according to the invention. The GSHE is most useful in applications requiring granular starch hydrolysis to sugars, for example in the manufacture of glucose syrups and for grain processing in ethanol production.

EXPERIMENTAL

The following examples are provided in order to demonstrate and further illustrate certain preferred embodiments and aspects of the present invention and are not to be construed as limiting the scope thereof. Indeed, it is contemplated that these teachings will find use in further optimizing the process systems described herein.

In the disclosure and experimental section which follows, the following abbreviations apply: wt % (weight percent); ° C. (degrees Centigrade); rpm (revolutions per minute); $H_2O$ (water); $dH_2O$ (deionized water); aa (amino acid); bp (base pair); kb (kilobase pair); kD (kilodaltons); g (grams); μg (micrograms); mg (milligrams); μL (microliters); ml and mL (milliliters); mm (millimeters); μm (micrometer); M (molar); mM (millimolar); μM (micromolar); U (units); V (volts); MW (molecular weight); sec (seconds); min(s) (minute/minutes); hr(s) (hour/hours); PAGE (polyacrylamide gel electrophoresis); DO (dissolved oxygen); phthalate buffer (sodium phthalate in water, 20 mM, pH 5.0); PBS (phosphate buffered saline [150 mM NaCl, 10 mM sodium phosphate buffer, pH 7.2]); SDS (sodium dodecyl sulfate); Tris (tris(hydroxymethyl)aminomethane); w/v (weight to volume); w/w (weight to weight); v/v (volume to volume); Genencor (Genencor International, Inc., Palo Alto, Calif.); and Shin Nihon (Shin Nihon, Japan).

Example 1

Cloning the *H. Grisea* Var. *Thermoidea* GSHE Gene

Genomic DNA (SEQ ID NO:1) was extracted from frozen *Scytalidium thermophilum* (ATCC 16453, anamorph, *H. grisea* var. *thermoidea*) mycelia. The frozen mycelia were ground with dry ice in a coffee grinder and the DNA was extracted by the EasyDNA protocol (Invitrogen). An extra chloroform/phenol/isoamyl alcohol extraction was added to the standard protocol. PCR primers were designed, based on the NCBI database accession #M89475 sequence. The forward primer contained a motif for directional cloning into the pENTR/D vector (Invitrogen).

The sequence of the RSH003f primer was CAACATG-CATACCTTCTCCAAGCTCCTC (SEQ ID NO. 7) and the sequence of the RSH004r primer was TTAACGCCAC-GAATCATTCA CCGTC (SEQ ID NO. 8).

The PCR product was cloned into pENTR/D, according to the Invitrogen Gateway system protocol. The vector was then transformed into chemically competent Top10 *E. coli* (Invitrogen) with kanamycin selection. Plasmid DNA from several clones was restriction digested to confirm the correct size insert. The gla1 insert was sequenced (Sequetech, Mountain View, Calif.) from several clones. Plasmid DNA from one clone, pENTR/D_N13, was added to the LR clonase reaction (Invitrogen Gateway system) with pTrex3g/amdS destination vector DNA. Recombination, in the LR clonase reaction, replaced the CmR and ccdB genes of the destination vector with the *H. grisea* gla1 from the pENTR/D vector. This recombination directionally inserted gla1 between the cbhI promoter and terminator of the destination vector. Recombination site sequences of 48 and 50 bp remained upstream and downstream, respectively, of gla1. An aliquot of the LR clonase reaction was transformed into chemically competent Top10 *E. coli* and grown overnight with carbenicillin selection. Plasmid DNA, from several clones, was digested with appropriate restriction enzymes to confirm the correct insert size. Plasmid DNA from clone, pTrex3g_N13 (see FIGS. 3 and 4) was digested with Xba1 to release the expression cassette including the cbhI promoter:gla1:cbhI terminator: amdS. This 6.6 kb cassette was purified by agarose gel extraction using standard techniques and transformed into a strain of *T. reesei* derived from the publicly available strain QM6a, as further described below.

The cassette was sequenced by Sequetech, Mountain View, Calif. and the DNA for GSHE is illustrated in FIG. 1 (SEQ ID NO:1) and the amino acid sequence illustrated in FIG. 2 (SEQ ID NOs:2 and 3).

Example 2

Transformation of *T. Reesei*

Approximately 2 $cm^2$ of a plate of sporulated mycelia (grown on a PDA plate for 5 days at 30° C.) was inoculated into 50 ml of YEG (5 g/L yeast extract plus 20 g/L glucose) broth in a 250 ml, 4-baffle shake flask and incubated at 37° C. for 16-20 hours at 200 rpm. The mycelia were recovered by transferring the liquid volume into 50 ml conical tubes and spinning at 2500 rpm for 10 minutes. The supernatant was decanted. The mycelial pellet was transferred into a 250 ml, 0.22 micron CA Corning filter bottle containing 40 ml of filtered β-D-glucanase solution and incubated at 30° C., 200 rpm for 2 hrs to generate protoplasts for transformation.

Protoplasts were harvested by filtration through sterile miracloth into a 50 ml conical tube. They were pelleted by spinning at 2000 rpm for 5 minutes and aspirated. The protoplast pellet was washed once with 50 ml of 1.2 M sorbitol, spun down, aspirated, and washed with 25 ml of sorbitol/$CaCl_2$. Protoplasts were counted and then pelleted at 2000 rpm for 5 min, the supernate was decanted, and the protoplast pellet was resuspended in an amount of sorbitol/$CaCl_2$ sufficient to generate a protoplast concentration of $1.25 \times 10^8$ protoplasts per ml, generating a protoplast solution.

Aliquots of up to 20 μg of expression vector DNA (in a volume no greater than 20 μl) were placed into 15 ml conical tubes and the tubes were put on ice. Then 200 μl of the protoplast suspension was added along with 50 μl PEG solution to each transformation aliquot. The tubes were mixed gently and incubated on ice for 20 min. PEG solution (2 ml) was added to the transformation aliquot tubes, and these were incubated at room temperature for 5 minutes. Sorbitol/CaCl$_2$ (4 ml) solution was added to the tubes (generating a total volume of 6.2 ml). The transformation mixture was divided into 3 aliquots each containing about 2 ml. An overlay mixture was created by adding each of these three aliquots to three tubes of melted top agar (kept molten by holding at 50° C.) and this overlay mixture was poured onto a transformation plate. The transformation plates were then incubated at 30° C. for four to seven days.

The transformation was performed with amdS selection. Acetamide/sorbitol plates and top agar were used for the transformation. Top agar was prepared by the same Sorbitol/acetamide agar recipe as the plates, except that low melting agarose was used in place of Noble agar. Transformants were purified by transfer of isolated colonies to fresh selective media containing acetamide (i.e., Sorbitol/acetamide agar, without sorbitol).

With reference to the examples the solutions were prepared as follows.

1) 40 ml β-D-glucanase solution was made up in 1.2M sorbitol and included 600 mg β-D-glucanase (InterSpex Products Inc., San Mateo, Calif.) and 400 mg MgSO$_4$.7H$_2$O.

2) 200 ml PEG mix contained 50 g PEG 4000 (BDH Laboratory Supplies Poole, England) and 1.47 g CaCl$_2$.2H$_2$O made up in dH$_2$O.

3) Sorbitol/CaCl$_2$ contained 1.2M sorbitol and 50 mM CaCl$_2$.

4) Acetamide/sorbitol agar:
Part 1—0.6 g acetamide (Aldrich, 99% sublime), 1.68 g CsCl, 20 g glucose, 20 g KH$_2$PO$_4$, 0.6 g MgSO$_4$.7H$_2$O, 0.6 g CaCl$_2$.2H$_2$O, 1 ml 1000× salts (see below), adjusted to pH 5.5, brought to volume (300 mls) with dH$_2$O, filter sterilized.
Part II—20 g Noble agar and 218 g sorbitol brought to volume (700 mls) with dH$_2$O and autoclaved.
Part II was added to part I for a final volume of 1 L.

5) 1000× Salts—5 g FeSO$_4$.7H$_2$O, 1.6 g MnSO$_4$.H$_2$O, 1.4 g ZnSO$_4$.7H$_2$O, 1 g CoCl$_2$.6H$_2$O were combined and the volume was brought to 1 L with dH$_2$O. The solution was filter sterilized.

Example 3

Fermentation of *T. Reesei* Transformed with the *H. Grisea* Var. *Thermoidea* GSHE Gene In general, the fermentation protocol as described in Foreman et al. (Foreman et al. (2003) *J. Biol. Chem.* 278:31988-31997) was followed. More specifically, duplicate fermentations were run for each of the strains displayed in FIG. 5. 0.8 L of Vogels minimal medium (Davis et al., (1970) Methods in Enzymology 17A, pg 79-143 and Davis, Rowland, NEUROSPORA, CONTRIBUTIONS OF A MODEL ORGANISM, Oxford University Press, (2000)) containing 5% glucose was inoculated with 1.5 ml frozen spore suspension. After 48 hours, each culture was transferred to 6.2 L of the same medium in a 14 L Biolafitte fermenter. The fermenter was run at 25° C., 750 RPM and 8 standard liters per minute airflow. One hour after the initial glucose was exhausted, a 25% (w/w) lactose feed was started and fed in a carbon limiting fashion to prevent lactose accumulation. The concentrations of glucose and lactose were monitored using a glucose oxidase assay kit or a glucose hexokinase assay kit with beta-galactosidase added to cleave lactose, respectively (Instrumentation Laboratory Co., Lexington, Mass.). Samples were obtained at regular intervals to monitor the progress of the fermentation. Collected samples were spun in a 50 ml centrifuge tube at ¾ speed in an International Equipment Company (Needham Heights, Mass.) clinical centrifuge.

Sample supernatants were run of 4-12% BIS-TRIS SDS-PAGE gels, under reducing conditions with MOPS (morpholinepropanesulfonic acid) SDS running buffer and LDS sample buffer. The results are provided in FIG. 5. Lanes 3, 4 and 5 illustrate a 68 kD rGSHE band at different time periods.

Example 4

Assay of GSHE Activity from Transformed *Trichoderma Reesei* Clones

Enzyme Activity

GSHE activity was determined as milligrams (mg) of reducing sugars released (measured as glucose equivalent) per minute (min) during an incubation of 5 ml of 10% granular cornstarch in a 0.1 M acetate buffer, pH 4.5, 50° C. with an aliquot of the enzyme preparation. One unit of GSHE is defined as 1.0 mg of reducing sugar released per min under the assay conditions.

Native GSHE (nGSHE) from *Humicola grisea* var. *thermoidea* and recombinant GSHE produced from *T. reesei* were purified by standard techniques using hydrophobic interaction chromatography using phenyl-sepharose (Amersham Biosciences, Piscataway, N.J.) followed by ion exchange chromatography using SP-sepharose (Amersham Biosciences, Piscataway, N.J.). The recombinant GSHE initially expressed by *T. reesei* clones included two protein peak fractions in about equal concentrations. These peaks were labeled rGSHE1 and rGSHE2. The two peaks differed in mass by 1500 D and by 0.3 pH units as measured by matrix assisted laser desorption and ionization (MALDI-TOF) on a voyageur mass spectrometer (Applied Biosystems, Foster City, Calif.) and an isoelectric focusing gel (SERVA Electrophoresis, GmbH, Heidelberg, Germany) according to manufacturer directions. Both rGSHE1 and rGSHE2 have the same specific activity as measured by the raw starch hydrolyzing assay and protein measurements using a MicroBCA protein assay kit (Pierce, Rockford, Ill.) and the percent solution extinction coefficient (A280 0.1%=1.963). After a period of time, measured at approximately 72 hours after initial rGSHE expression, only one form of rGSHE is represented (rGSHE3). (See Table 1).

TABLE 1

| Source of GSHE | Specific Activity GSHE Units/mg | % total carbohydrate |
|---|---|---|
| Native GSHE | 9.0 | 1.12 |
| rGSHE1/rGSHE2 | 8.0/8.0 | 2.70 |
| rGSHE3 | 8.0 | 0.57 |

The % carbohydrate (CHO) of the GSHEs was determined by acid hydrolysis using 4N trifluoroacetic acid at 100° C. for 5 hrs and measurements were made of the released reducing sugars using parahydroxybenzoic acid hydrazide.

When initially expressed, the glycosylation of rGSHE1 and rGSHE2 was 2.70% of the total carbohydrate. However, after 72 hours, the level of glycosylation of rGSHE3 found in the medium was 0.57% total CHO. The level of glycosylation of native GSHE was 1.12%.

Example 5

Comparison of Native GSHE from *H. Grisea* Var. Thermoidea and Recombinantly Expressed *H. Grisea* Var. Thermoidea GSHE in *Trichoderma Reesei*

A. pH Stability was Determined from pH 3 to 7

The collected samples of recombinantly produced GSHE as described above in example 3 and samples of native GSHE were diluted to equal protein concentrations with 20 mM acetate buffer at pH 4.5. Reactions were then run in 100 mM citrate/NaOH buffers at 50° C. for 30 minutes at pH levels 3 to 7.

1.0 ml of the reaction was then added to 5 ml of 10% corn starch (Cargill Foods, Minneapolis, Minn.) in 100 mM acetate, pH 4.5 in sample tubes. The tubes were shaken at 50° C. for 20 minutes. Then 0.5 ml 2.0% NaOH was added. Tubes were spun and 0.5 ml of the supernatant was assayed for reducing sugars using the Dinitro Salicylic acid (DNS) assay (Goto et al., (1994) supra).

Figure 8A:
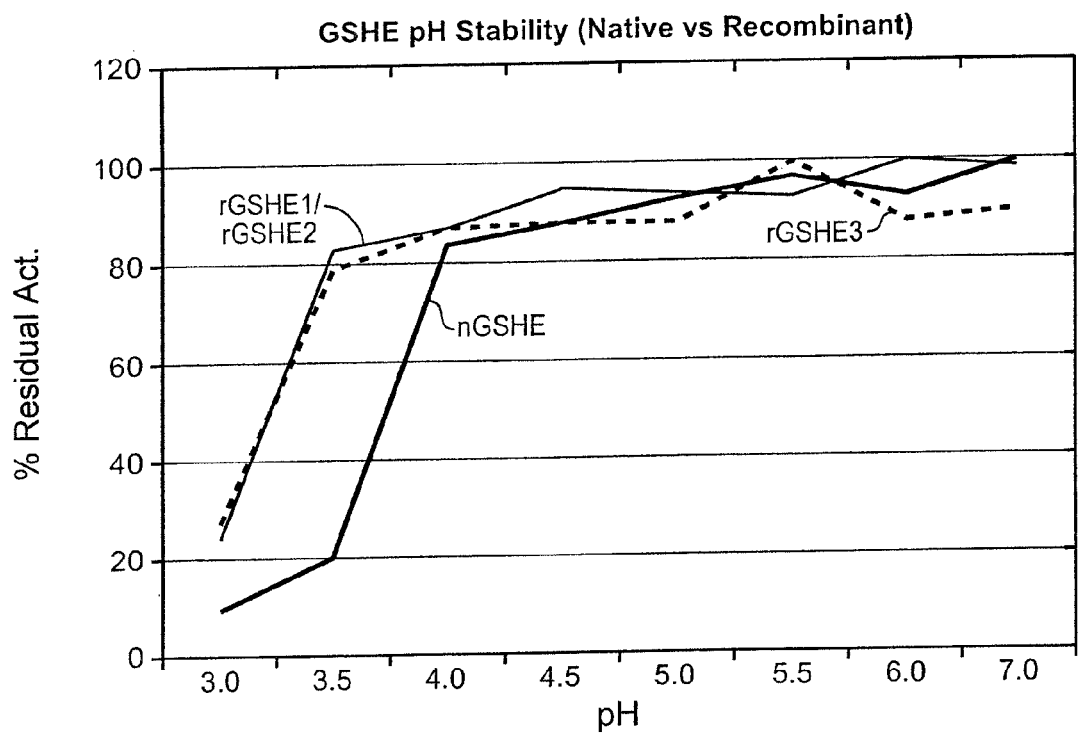
FIGS. 8A and 8B illustrate the pH stability as % residual activity for the native *Humicola grisea* var. *thermoidea* GSHE (nGSHE) and the expressed *H. grisea* var. *thermoidea* GSHE (rGSHE) in the *T. reesei* host (SEQ ID NO:3), as described in Example 5.

The results of the assay are depicted in FIG. 8A. The recombinantly produced GSHE exhibited about 80% residual activity at pH 3.5. In comparison, the corresponding native GSHE exhibited only about 20% residual activity. At pH 4.0 both the recombinantly produced GSHE and the native GSHE exhibited about 82% residual activity and at pH 5.5 both enzymes exhibited between about 90 to 100% residual activity.

Figure 8B:
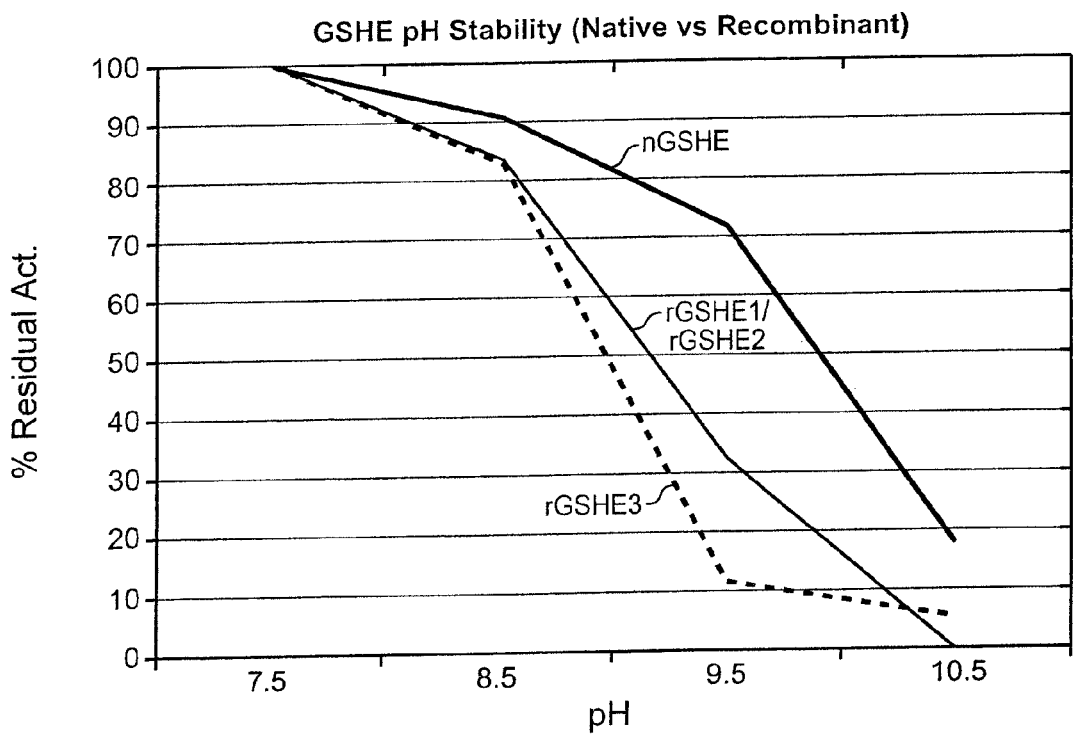

Stability was also measured at pH 7.5 to 10.5 using the methods as described above. However, the buffer was 100 mM boric acid/NaOH buffer. As exhibited in FIG. 8B, at pH 7.5 both enzymes exhibited about 100% residual activity. At pH 8.5 recombinantly produced GSHE exhibited about 82% residual activity and the native GSHE exhibited about 90% residual activity. At pH 9.5 the % residual activity of recombinantly produced GSHE was substantially less than the native GSHE. (10% compared to 72%, respectively).

B. Profile of Activity as a Function of Temperature

Temperature stability was determined at pH 5.75. Using essentially the same procedures as described above for the pH stability studies, enzyme samples were diluted to equal protein concentrations in a 100 mM acetate buffer and then 1.0 ml of the diluted enzymes was exposed to a water bath temperature of 40° C., 50° C., 60° C. and 70° C. for 10 minutes and assayed as described above in the pH stability studies. The results are presented in Table 2.

TABLE 2

| GSHE Source | Temp ° C. | % Residual Activity |
|---|---|---|
| Native GSHE | 40 | 100 |
|  | 50 | 95 |
|  | 60 | 90 |
|  | 70 | 0 |
| Recombinant GSHE | 40 | 100 |
|  | 50 | 93 |
|  | 60 | 92 |
|  | 70 | 0 |

% residual activity means the % difference referenced to 100% at pH 4.0

The profile of activity as a function of temperature of the recombinantly produced GSHE is similar to that of the corresponding native GSHE.

c. Hydrolysis of Granular Corn Starch by nGSHE And rGSHE

Figure 9:
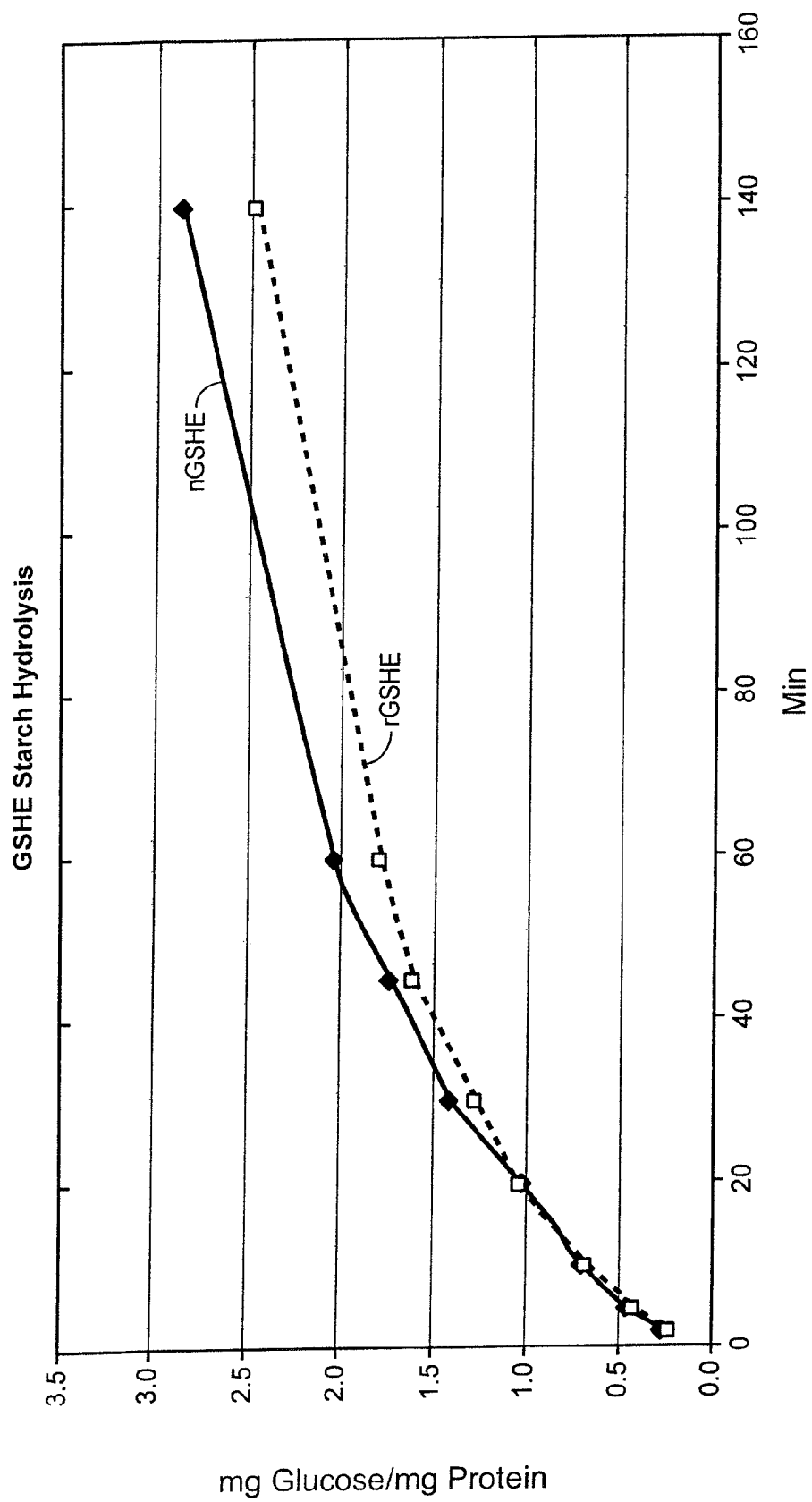
FIG. 9 illustrates the hydrolysis of corn starch measured as mg glucose/mg protein over time for native *Humicola grisea* var. *thermoidea* GSHE and the expressed *H. grisea* var. *thermoidea* GSHE in the recombinant *T. reesei* host, as described in Example 5.

Both Native GSHE from *H. Grisea* Var. Thermoidea (nGSHE) and recombinantly expressed *H. grisea* var. *thermoidea* (rGSHE) in *Trichoderma reesei* were diluted to equal protein concentrations in pH 4.5 acetate buffer. One ml of the dilution was added to a 10% corn starch (Cargill Foods, Minneapolis, Minn.) slurry in 20 mM pH 4.5 acetate buffer and shaken at 350 rpm at 50° C. At designated time intervals 100 μL of slurry was removed and added to 10 μL of 2% NaOH. The sample was spun and the supernatant was assayed for glucose (mg glucose/mg protein) using the glucose oxidase reagent in a Monarch clinical analyzer (Instrumentation Laboratory, Lexington, Mass.). As shown in FIG. 9 the hydrolysis of corn starch was slightly lower for the rGSHE compared to the nGSHE.

Example 6

Cloning the *Aspergillus Awamori* Var. *Kawachi* GSHE Gene

Genomic DNA was extracted from frozen mycelia of a strain of *A. awamori* var. *kawachi* according to the methods described in Example 1. The PCR primer sequences were designed based on the published sequence of the *A. awamori* var. *kawachi* glucoamylase GAI (Hayashida, et al. (1989) *Agric. Biol. Chem.* 53:923-929). This GAI is a GSHE. The following primers were used: the RSH10f primer having the sequence, CAC CAT GTC GTT CCG ATC TCT TCT C (SEQ ID NO:9), which includes the Gateway (Invitrogen) directional cloning motif CACC and the RSH11r primer having the sequence, CTA CCG CCA GGT GTC GGT CAC (SEQ ID NO:10).

The DNA sequence is provided in FIG. 6 (SEQ ID NO:4). The encoded GSHE polypeptide sequence, including the signal peptide, is provided in FIG. 7A (SEQ ID NO:5) and the mature protein sequence is provided in FIG. 7B (SEQ ID NO:6).

Figure 3:
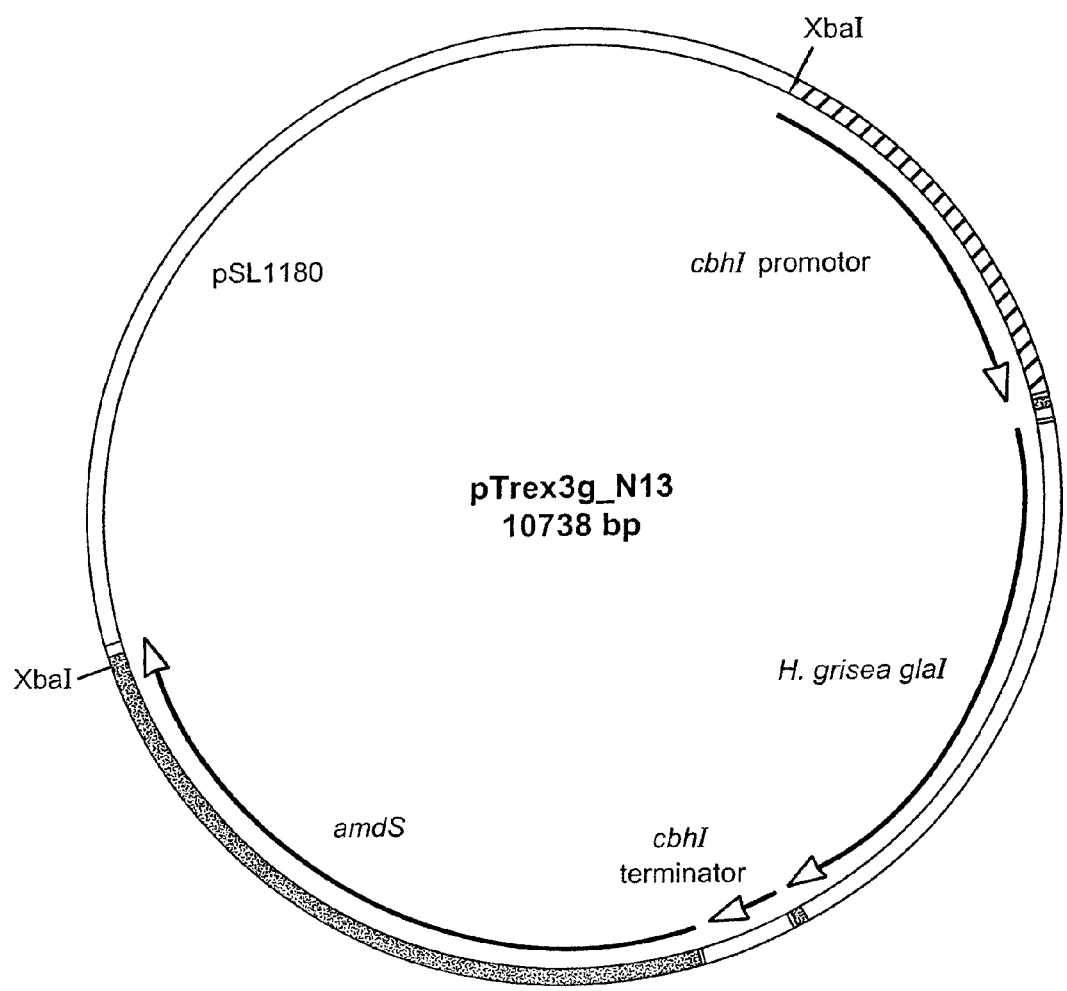
FIG. 3 provides a map of pTrex3g_N13 plasmid, which was used for expression of the nucleic acid encoding the *Humicola grisea* GSHE and which contains the Xba1 sites flanking the fungal expression vector wherein
 a) cbhI promoter is the *Trichoderma reesei* cellobiohydrolase promoter,
 b) *H. grisea* gla1 is the polynucleotide encoding the *Humicola grisea* GSHE of SEQ ID NO:3,
 c) cbhI terminator is the *Trichoderma reesei* cellobiohydrolase terminator and
 d) amdS is an *Aspergillus nidulans* acetamidase marker gene.

The 2.16 kb PCR product was gel-purified (Gel Purification kit, Qiagen) and cloned into pENTR/D (Invitrogen), according to the Gateway system protocol. The vector was then transformed into chemically competent Top10 *E. coli* (Invitrogen) with kanamycin selection. Plasmid DNA from several clones was restriction digested to confirm the correct size insert. The GAI gene insert was sequenced (Sequetech, Mountain View, Calif.) from several clones (SEQ ID NO:4). Plasmid DNA from one clone, pENTR/D_Ak33xx#1, was added to the LR clonase reaction (Invitrogen Gateway system) with the pTrex3g/amdS destination vector DNA. Recombination, in the LR clonase reaction, replaced the Cm$^R$ and ccdB genes of the destination vector with the *A. kawachi* GAI from the pENTR/D vector. This recombination directionally inserted GAI between the cbhI promoter and terminator of the destination vector. AttB recombination site sequences of 48 and 50 bp remained upstream and downstream, respectively, of the glucoamylase. Reference is made to FIG. 3, wherein the *H. grisea* gla1 has been replaced by the *A. kawachi* GAI in this example. Two microliters of the LR clonase reaction were transformed into chemically competent Top10 *E. coli* and grown overnight with carbenicillin selection. Plasmid DNA from several clones was digested with XbaI to confirm the insert size. Plasmid DNA from clone, pTrex3g_Akxx #3 was digested with XbaI to release the expression cassette including the cbhI promoter:GAI:cbhI terminator:amdS. This 6.7 kb cassette was purified by agarose extraction using standard techniques and transformed into a strain of *T. reesei* derived from the publicly available strain QM6a.

Example 7

Transformation of *T. Reesei* with the *A. Awamori* Var. *Kawachi* GSHE Gene A *Trichoderma reesei* spore suspension was spread onto the center ~6 cm diameter of an MABA transformation plate (150 μl of a 5×10$^7$-5×10$^8$ spore/ml suspension). The plate was then air dried in a biological hood. Stopping screens (BioRad 165-2336) and macrocarrier holders (BioRad 1652322) were soaked in 70% ethanol and air dried. DriRite desiccant was placed in small Petri dishes (6 cm Pyrex) and overlaid with Whatman filter paper. The macrocarrier holder containing the macrocarrier (BioRad 165-2335) was placed flatly on top of filter paper and the Petri dish lid replaced.

A tungsten particle suspension was prepared by adding 60 mg tungsten M-10 particles (microcarrier, 0.7 micron, Biorad #1652266) to an Eppendorf tube. One ml ethanol (100%) was added. The tungsten was vortexed in the ethanol solution and allowed to soak for 15 minutes. The Eppendorf tube was microfuged briefly at maximum speed to pellet the tungsten. The ethanol was decanted and washed three times with sterile distilled water. After the water wash was decanted the third time, the tungsten was resuspended in 1 ml of sterile 50% glycerol. The tungsten was prepared fresh every two weeks.

The transformation reaction was prepared by adding 25 μl of suspended tungsten to a 1.5 ml Eppendorf tube for each transformation. Subsequent additions were made in order, 0.5-5 μl DNA (0.2-1 μg/μl), 25 μl 2.5M CaCl$_2$, 10 μl 0.1 M spermidine. The reaction was vortexed continuously for 5-10 minutes, keeping the tungsten suspended. The Eppendorf tube was then microfuged briefly and decanted. The tungsten pellet was washed with 200 μl of 70% ethanol, microfuged briefly to pellet and decanted. The pellet was washed with 200 μl of 100% ethanol, microfuged briefly to pellet, and decanted. The tungsten pellet was resuspended, by pipetting, in 24 μl 100% ethanol. The Eppendorf tube was placed in an ultrasonic water bath for 15 seconds and 8 μl aliquots were transferred onto the center of the desiccated macrocarriers. The macrocarriers were left to dry in the desiccated Petri dishes.

A He tank was turned on to 1500 psi. 1100 psi rupture discs (BioRad 165-2329) were used in the Model PDS-1000/He Biolistic Particle Delivery System (BioRad). When the tungsten solution was dry, a stopping screen and the macrocarrier holder were inserted into the PDS-1000. An MABA plate, containing the target *T. reesei* spores, was placed 6 cm below the stopping screen. A vacuum of 29 inches Hg was pulled on the chamber and held. The He Biolistic Particle Delivery System was fired. The chamber was vented and the MABA plate removed for incubation, 28° C. for 5-7 days.

With reference to Example 7 the were prepared as follows.

| Modified amdS Biolistic agar (MABA) | per liter |
|---|---|
| Part I, make in 500 ml dH$_2$O | |
| 1000x salts | 1 ml |
| Noble agar | 20 g |
| pH to 6.0, autoclave | |
| Part II, make in 500 ml dH$_2$O | |
| Acetamide | 0.6 g |
| CsCl | 1.68 g |
| Glucose | 20 g |
| KH$_2$PO$_4$ | 15 g |
| MgSO$_4$•7H$_2$O | 0.6 g |
| CaCl$_2$•2H$_2$O | 0.6 g |
| pH to 4.5, 0.2 micron filter sterilize; leave in 50° C. oven to warm, add to Part I, mix, pour plates. | |

| 1000x Salts | per liter |
|---|---|
| FeSO$_4$•7H$_2$O | 5 g |
| MnSO$_4$•H$_2$O | 1.6 g |
| ZnSO$_4$•7H$_2$O | 1.4 g |
| CoCl$_2$•6H$_2$O | 1 g |
| 0.2 micron filter sterilize | |

Expression of rGSHE (*A. awamori* var. *kawachi* GSHE expressed in *T. reesei*) was determined as described above for expression of *H. grisea* var. *thermoidea* in Examples 3 and 4. The level of expression was determined to be greater than 1 g/L (data not shown). FIG. 10 provides the results of a SDS-PAGE gel illustrating the expression of *Aspergillus awamori* var. *kawachi* GSHE in the *T. reesei* host.

It is claimed:

1. A method for producing a granular starch hydrolyzing enzyme having glucoamylase activity (GSHE) in a filamentous fungal host cell comprising
   a) transforming a filamentous fungal host cell with a DNA construct comprising a promoter having transcriptional activity in the filamentous fungal host cell operably linked to a heterologous polynucleotide encoding the GSHE polypeptide of SEQ ID NO: 6,
   b) cultivating the transformed filamentous fungal host cell in a suitable culture medium to allow expression of said GSHE, and
   c) producing the GSHE.

2. The method according to claim 1 further comprising recovering the produced GSHE.

3. The method according to claim 1, wherein the filamentous fungal host cell is a *Trichoderma* cell.

4. The method according to claim 3, wherein the *Trichoderma* cell is a *T. reesei* cell.

5. The method according to claim 1, wherein the filamentous fungal host cell is an *Aspergillus* cell.

6. The method according to claim 5, wherein the *Aspergillus* cell is an *A. awamori*, *A. niger* or *A. oryzae* cell.

7. The method according to claim 1, wherein one or more genes encoding cellulytic enzymes has been deleted in the filamentous fungal host cell.

8. The method according to claim 1, wherein a level of glycosylation of the expressed GSHE from the transformed filamentous fungal host cell is less than the level of glycosylation of the GSHE expressed in a native fungal host.

9. The method according to claim 8, wherein the native fungal host is a strain of *Humicola grisea*.

10. The method according to claim 1, wherein the amount of GSHE expressed is greater than 1.0 g/L of culture media.

11. The method according to claim 1, wherein the amount of GSHE expressed is greater than 10 g/L of culture media.

12. The method according to claim 1, wherein at a pH level of about 3.0 to 4.0 enzyme activity is greater for the produced GSHE than enzyme activity of the corresponding GSHE expressed and produced in a native fungal host.

13. The method according to claim 1, wherein the transformed fungal host cell is cultured under continuous fermentation conditions.

14. The method according to claim 1, wherein the transformed fungal host is cultured under batch fermentation conditions.

15. A recombinant *Trichoderma* cell comprising a heterologous polynucleotide encoding a granular starch hydrolyzing enzyme having glucoamylase activity (GSHE), wherein the GSHE comprises the amino acid sequence of SEQ ID NO:6.

16. The recombinant *Trichoderma* cell of claim 15, wherein the *Trichoderma* cell is a *T. reesei* cell.

17. The recombinant *Trichoderma* cell of claim 15, wherein one or more genes encoding cellulytic enzymes has been deleted from the *Trichoderma* cell.

18. The recombinant cell of claim 15, wherein the GSHE has the amino acid sequence of SEQ ID NO: 6.

19. The method according to claim 1 further comprising recovering the produced GSHE.

* * * * *